US011173259B2

United States Patent
Calderon Oliveras et al.

(10) Patent No.: US 11,173,259 B2
(45) Date of Patent: Nov. 16, 2021

(54) DRUG DELIVERY DEVICE WITH ELECTRONICS AND POWER MANAGEMENT

(71) Applicant: Norton (Waterford) Limited, Waterford (IE)

(72) Inventors: Enrique Calderon Oliveras, Barcelona (ES); Amir Kesten, Har Adar (IL)

(73) Assignee: Norton (Waterford) Limited, Waterford (IE)

( * ) Notice: Subject to any disclaimer, the term of this patent is extended or adjusted under 35 U.S.C. 154(b) by 0 days.

(21) Appl. No.: 16/921,193

(22) Filed: Jul. 6, 2020

(65) Prior Publication Data

US 2021/0001061 A1    Jan. 7, 2021

Related U.S. Application Data

(60) Provisional application No. 62/870,894, filed on Jul. 5, 2019.

(51) Int. Cl.
    *A61M 15/00* (2006.01)

(52) U.S. Cl.
    CPC ........ *A61M 15/008* (2014.02); *A61M 15/009* (2013.01); *A61M 2205/18* (2013.01);
    (Continued)

(58) Field of Classification Search
    CPC .............. A61M 15/008; A61M 15/009; A61M 2205/18; A61M 2205/3561;
    (Continued)

(56) References Cited

U.S. PATENT DOCUMENTS

| 8,424,517 B2 | 4/2013 | Sutherland et al. |
| 8,464,707 B2 | 6/2013 | Jongejan et al. |

(Continued)

FOREIGN PATENT DOCUMENTS

| WO | 2016043601 A1 | 3/2016 |
| WO | 2017141194 A1 | 8/2017 |

(Continued)

OTHER PUBLICATIONS

Faiz, Mohammad, et al., "Data Synchronization in distributed Client-Server Applications", IEEE International Conference on Engineering and Technology (ICETECH), IEEE, XP032962273, DOI: 10.1109/ICTECH.2016.569323, Mar. 17, 2016, 611-616.

*Primary Examiner* — Timothy A Stanis
(74) *Attorney, Agent, or Firm* — Flaster Greenberg, P.C.

(57) ABSTRACT

A system may limit the number of times an inhalation device transmits inhalation data to a single time to reduce the battery usage of the inhalation device. The system may include an inhalation device that has medicament and an electronics module. The system may limit the number of times the inhalation device transmits new inhalation data to any mobile device to a single time by causing the server to receive the new inhalation data from one of the mobile devices and causing the server to transmit the new inhalation data to other of the mobile devices prior to the other mobile devices transmitting a request for the new inhalation data to the inhalation device. The inhalation device may include a Quick Response (QR) code, and a mobile application may determine at least one of a medication type or a number of doses of the inhalation device from the QR code.

24 Claims, 6 Drawing Sheets

(52) U.S. Cl.
CPC .............. *A61M 2205/3561* (2013.01); *A61M 2205/6009* (2013.01); *A61M 2205/609* (2013.01); *A61M 2205/6063* (2013.01); *A61M 2205/8212* (2013.01)

(58) Field of Classification Search
CPC .. A61M 2205/6009; A61M 2205/6063; A61M 2205/609; A61M 2205/8212
See application file for complete search history.

(56) References Cited

U.S. PATENT DOCUMENTS

| | | | |
|---|---|---|---|
| 9,035,765 B2 * | 5/2015 | Engelhard ............ | A61J 7/0418 340/539.18 |
| 9,468,729 B2 | 10/2016 | Sutherland et al. | |
| 9,550,031 B2 | 1/2017 | Van Sickle et al. | |
| 9,555,200 B2 | 1/2017 | Hosemann et al. | |
| 9,692,829 B2 | 6/2017 | Starr et al. | |
| 9,734,302 B2 | 8/2017 | Nielsen et al. | |
| 9,872,964 B2 | 1/2018 | Cline et al. | |
| 9,943,656 B2 | 4/2018 | Shears et al. | |
| 10,019,555 B2 * | 7/2018 | Manice ............ | A61M 15/0083 |
| 10,173,020 B2 | 1/2019 | Sutherland et al. | |
| 10,220,166 B2 | 3/2019 | Van Sickle et al. | |
| 10,255,412 B2 | 4/2019 | Hogg et al. | |
| 10,300,227 B2 | 5/2019 | Sutherland | |
| 10,388,412 B1 | 8/2019 | Koblenski et al. | |
| 10,460,835 B2 | 10/2019 | Semen et al. | |
| 10,603,450 B2 | 3/2020 | Sutherland | |
| 10,668,232 B2 | 6/2020 | Sutherland et al. | |
| 10,726,954 B2 | 7/2020 | Su et al. | |
| 10,828,434 B2 | 11/2020 | Sutherland | |
| 2003/0113269 A1 * | 6/2003 | Gavin ..................... | A61P 11/06 424/45 |
| 2008/0230057 A1 | 9/2008 | Sutherland et al. | |
| 2009/0221308 A1 | 9/2009 | Lerner et al. | |
| 2010/0250280 A1 | 9/2010 | Sutherland et al. | |
| 2014/0182584 A1 | 7/2014 | Sutherland et al. | |
| 2016/0036898 A1 * | 2/2016 | Curtis ................. | G09B 19/003 709/203 |
| 2016/0144141 A1 | 5/2016 | Sabharwal et al. | |
| 2017/0076065 A1 * | 3/2017 | Darr ....................... | G16H 70/40 |
| 2017/0109493 A1 | 4/2017 | Hogg et al. | |
| 2017/0161461 A1 | 6/2017 | Delangre et al. | |
| 2017/0235918 A1 | 8/2017 | Hagen et al. | |
| 2017/0290527 A1 * | 10/2017 | Morrison ............ | A61M 16/021 |
| 2017/0325734 A1 | 11/2017 | Sutherland et al. | |
| 2018/0093053 A1 | 4/2018 | Turner et al. | |
| 2018/0140786 A1 * | 5/2018 | Calderon Oliveras ...................... | A61M 15/0083 |
| 2018/0221600 A1 | 8/2018 | Shears et al. | |
| 2018/0236187 A1 | 8/2018 | Jung et al. | |
| 2018/0308572 A1 | 10/2018 | Manice et al. | |
| 2018/0315498 A1 | 11/2018 | Starr et al. | |
| 2019/0001085 A1 | 1/2019 | Cottenden et al. | |
| 2019/0046074 A1 | 2/2019 | Sabharwal | |
| 2019/0060590 A1 | 2/2019 | Starr et al. | |
| 2019/0102522 A1 | 4/2019 | Barrett et al. | |
| 2019/0105450 A1 | 4/2019 | Sutherland et al. | |
| 2019/0151577 A1 | 5/2019 | Jung et al. | |
| 2019/0175847 A1 | 6/2019 | Pocreva et al. | |
| 2019/0189258 A1 | 6/2019 | Barrett et al. | |
| 2019/0240430 A1 * | 8/2019 | Jackson ............ | A61M 15/008 |
| 2019/0272925 A1 | 9/2019 | Barrett et al. | |
| 2019/0298942 A1 | 10/2019 | Koblenski et al. | |
| 2019/0385727 A1 | 12/2019 | Manice et al. | |
| 2020/0058403 A1 | 2/2020 | Barrett et al. | |
| 2020/0143939 A1 | 5/2020 | Semen et al. | |
| 2020/0316321 A1 | 10/2020 | Sutherland et al. | |

FOREIGN PATENT DOCUMENTS

| | | |
|---|---|---|
| WO | 2018104268 A1 | 6/2018 |
| WO | 2018160073 A1 | 9/2018 |
| WO | 2018200431 A1 | 11/2018 |
| WO | 2019022620 A1 | 1/2019 |
| WO | 2019180214 A1 | 9/2019 |
| WO | 2019193061 A1 | 10/2019 |
| WO | 2019209994 A1 | 10/2019 |
| WO | 2019226576 A1 | 11/2019 |

* cited by examiner

DRUG DELIVERY DEVICE WITH ELECTRONICS AND POWER MANAGEMENT

CROSS-REFERENCE TO RELATED APPLICATIONS

This application claims the benefit of Provisional U.S. Patent Application No. 62/870,894, filed Jul. 5, 2019, the disclosure of which is incorporated herein by reference in its entirety.

BACKGROUND

Drug delivery devices facilitate the delivery of medication into a patient's body via various routes of administration. Typical routes of administration include oral, topical, sublingual inhalation, injection and the like. The devices may be used to deliver medications for the treatment of various diseases, ailments and medical conditions. Inhalation devices, for example, may be used to treat asthma, chronic obstructive pulmonary disease (COPD) and cystic fibrosis (CF). While drug delivery devices may be designed to deliver an appropriate dose of medication to a patient as part of a therapeutic treatment, the effectiveness of the treatment may be influenced by non-physiological factors, such as the patient's adherence and compliance in using the device.

Drug delivery devices may be equipped with sensors to track adherence and compliance. For example, a device may include a sensor for detecting when the device was actuated to deliver a dose of medication and/or its orientation during actuation. This information may be stored in a local memory and subsequently communicated to another device, such as a smartphone, tablet or computer, for further processing. The device's actuation history may be compared to a dosing regimen prescribed by a physician to determine the patient's level of adherence. Other sensor data, such as the device's orientation during operation, may be reviewed to determine whether the patient is using the device in a compliant manner that facilitates proper delivery of the medication.

To support the addition of sensors and communication mechanisms, a drug delivery device may include a local power source. If the drug delivery device is portable, the local power source may be portable as well. For example, the local power source may be a small battery. Certain factors, such as size, weight, and/or cost, may limit the types of viable power sources for the device. Accordingly, a finite amount of power may be available when choosing a power source for a drug delivery device with electrical components.

SUMMARY

A system may be configured to limit the number of times an inhalation device (e.g., an inhaler) transmits inhalation data to a single instance to, for example, help reduce the battery usage of the inhalation device. The system may include one or more inhalation devices. The inhalation device may include a mouthpiece, medicament, and an electronics module. The medicament may include albuterol (such as albuterol sulfate, for example, at a concentration of 117 mcg), fluticasone (such as fluticasone propionate, for example 55 mcg, 113 mcg, or 232 mcg of fluticasone propionate per dose delivered by the inhalation device), beclomethasone dipropionate, or fluticasone (such as fluticasone propionate, for example 55 mcg, 113 mcg, or 232 mcg of fluticasone propionate per dose delivered by the inhalation device) combined with salmeterol (such as salmeterol xinafoate, for example, 14 mcg of salmeterol xinafoate per dose delivered by the inhalation device). The electronics module may include any combination of a controller (e.g., processor), a communication circuit (e.g., transmitter, receiver, transceiver, etc.), one or more sensors (e.g., a pressure sensor, a temperature sensor, a humidity sensor, an orientation sensor, etc.), a power supply, and/or memory. The system may also include a cloud-based system (e.g., a remote server, such as a database) that includes a connection (e.g., wire connection) to a public or private network to facilitate communication between the cloud-based system and one or more external devices (e.g., computers, tablets, mobile devices, etc.).

The system may also include a plurality of mobile devices, where each mobile device may include a communication circuit, memory, and a mobile application for the inhalation device (e.g., a mobile application that is specific to the inhalation device). The mobile devices (e.g., and respective mobile applications) may, for example, be controlled by different family members or health care providers, for example, to ensure that the user of the inhalation device is adherent and compliant with their medication schedule.

In some examples, a first mobile application that resides on a first mobile device may be configured to cause the first mobile device to transmit a request for inhalation data to the inhalation device, receive the inhalation data from the inhalation device (e.g., which may include a timestamp or counter value determined by the inhalation device), and transmit the inhalation data to the cloud-based system. In some examples, the request for the inhalation data may include an indication of the most recent inhalation data of the inhalation device that is stored on the first mobile device. Accordingly, the inhalation data received by the first mobile application from the inhalation device in response to the request may come before (e.g., postdate) the indication (e.g., the request) that was sent to the inhalation device. For example, the inhalation data may have occurred after (be subsequent to) any inhalation data that may already be stored on the first mobile device. For instance, the indication may include a timestamp of the most recent inhalation data of the inhalation device that is stored on the first mobile device, and the inhalation data sent in response to the request may be inhalation data that postdates the timestamp of the most recent inhalation data (e.g., only inhalation data that postdates the timestamp).

A second mobile application that resides on a different mobile device may be configured to cause the second mobile device to transmit a request to the cloud-based system, and configured to receive the inhalation data of the inhalation device from the cloud-based system in response to the request. The second mobile application may be configured to transmit the request to the cloud-based system prior to the second mobile device transmitting a request for the inhalation data to the inhalation device, thereby ensuring that the battery usage of the inhalation device is reduced. In some examples, the request may include an indication of a last synchronization time between the second mobile application and the inhaler. As such, the cloud-based system may be configured to send inhalation data that is subsequent to the last synchronization time between the second mobile application and the inhaler. In some examples, the second mobile application is configured to cause the second mobile device to transmit the request to the cloud-based system in response to detecting a user login event to the second mobile application, which is prior to the second mobile device transmitting the request for the inhalation data to the inhalation device.

In some embodiments, the first and second mobile application may be authenticated (e.g., associated with the inhalation device) by the cloud-based system prior to receiving the inhalation data from the inhalation device and/or prior to transmitting the inhalation data to or receiving the inhalation data from the cloud-based system. For example, the second mobile application may be configured to cause the second mobile device to transmit a product identification (ID) associated with the inhalation device or a patient ID associated with a patient of the inhalation device to the cloud-based system prior to the second mobile application receiving the inhalation data of the inhalation device from the cloud-based system. The mobile application may receive the product ID via a Quick Response (QR) code located on the inhalation device.

For instance, the system may include an inhalation device and one or more mobile applications. The system may be configured to authenticate the mobile applications (e.g., associate the mobile applications/mobile devices with the inhalation device), and be configured to confirm that the inhalation device is properly marked (e.g., confirm that the medication marked on the inhalation device is correct). The inhalation device may include medicament, an electronics module, and a QR code. The mobile application may reside on a mobile device that comprises a camera. The mobile application may be configured to determine information relating to the inhalation device (e.g., a medication type and/or a number of doses of the inhalation device) using the QR code. For example, the mobile application may be configured to access the camera to receive information related to the QR code, determine a product identifier (ID) of the inhalation device based on the QR code, and determine information relating to at least one of a medication type or a number of doses of the inhalation device based on the product ID. For example, the product ID may be a multiple character code that directly indicates the type of medication, the strength of the medication, and/or the number of doses in the inhalation device. Alternatively or additionally, the mobile application may send the product ID to the cloud-based system, and the cloud-based system may send the information relating to the inhalation device to the mobile application.

The mobile application may also be configured to determine a dosing schedule and/or one or more dosage reminders based on the QR code. For example, the mobile application may be configured to determine the dosing schedule of the inhalation device and/or the timing of dose reminders directly from the QR code (e.g., via a product ID). Alternatively or additionally, the mobile application may receive the dosing schedule and/or timing of dose reminders from the cloud-based system using on the product ID. The mobile application may be configured to provide one or more dosage reminders based on the dosing schedule.

In examples where the inhalation device includes the QR code, the inhalation device does not include an actuator, button, or switch to initiate a communication pairing process with the mobile device. Rather, the mobile application is configured to pair the mobile device (e.g., a communication module of the mobile device) to the inhalation device (e.g., the communication module of the inhalation device) using the QR code. For example, the mobile application may be configured to determine a communication passkey that is unique to the inhalation device based on the QR code, and cause the mobile device to transmit the communication passkey to the electronics module of the inhalation device to enable communication between the electronics module and the mobile application. The communication passkey may include the product ID. The communication passkey may, for example, include a Bluetooth Low Energy (BLE) passkey.

The mobile application may be configured to determine that the inhalation device is not compatible with the mobile application based on the medication type of the inhalation device, and display an error message based on the inhalation device being not compatible with the mobile application. Further, the mobile application may be configured to reject the pairing process of the inhalation device with the mobile device based on the inhalation device being not compatible with the mobile application.

DETAILED DESCRIPTION

Figure 1:
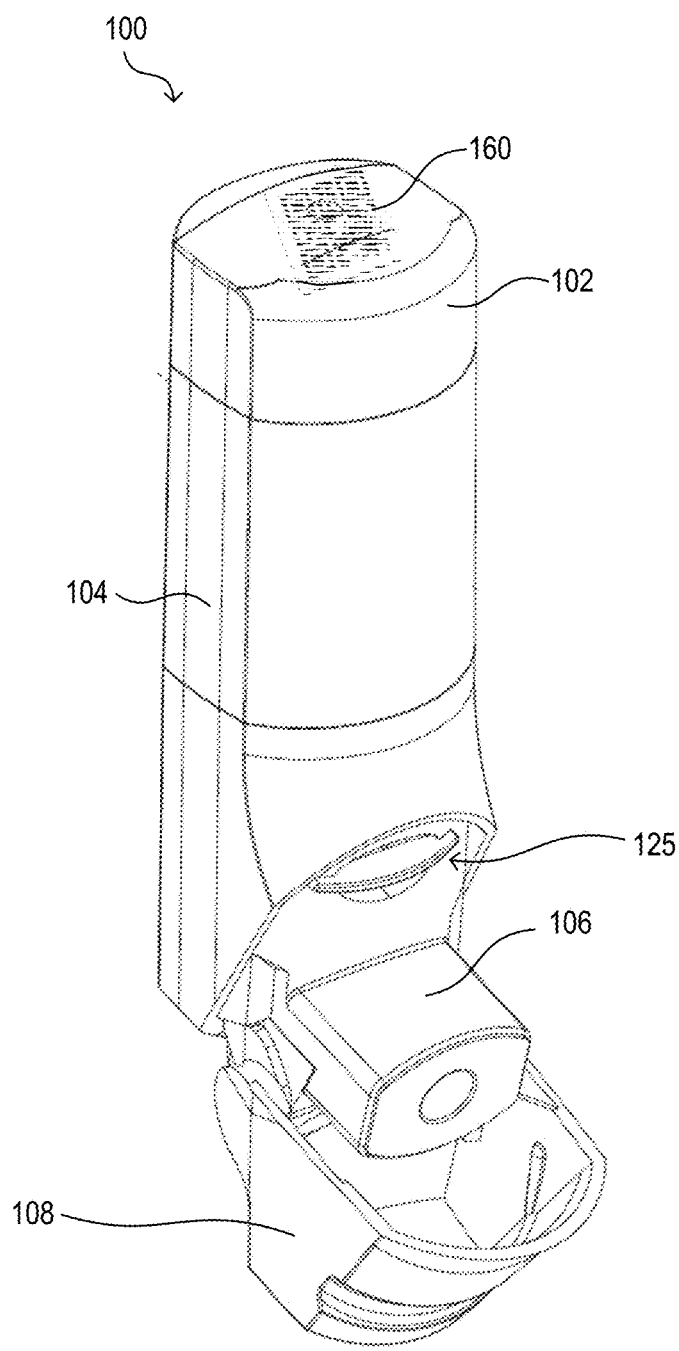
FIG. 1 is a front perspective view of an example inhalation device.

The present disclosure describes devices, systems and methods for sensing, tracking and/or processing usage conditions and parameters associated with a drug delivery device. The devices, systems and methods are described in the context of a breath-actuated inhalation device for delivering medication into a user's lungs. However, the described solutions are equally applicable to other drug delivery devices, such as an injector, a metered-dose inhaler, a nebulizer, a transdermal patch, or an implantable.

Asthma and COPD are chronic inflammatory disease of the airways. They are both characterized by variable and recurring symptoms of airflow obstruction and bronchospasm. The symptoms include episodes of wheezing, coughing, chest tightness and shortness of breath. The symptoms are managed by avoiding triggers and by the use of medicaments, particularly inhaled medicaments. The medicaments include inhaled corticosteroids (ICSs) and bronchodilators.

Inhaled corticosteroids (ICSs) are steroid hormones used in the long-term control of respiratory disorders. They function by reducing the airway inflammation. Examples include budesonide, beclomethasone (dipropionate/dipropionate HFA), fluticasone (propionate), mometasone (furoate), ciclesonide and dexamethasone (sodium). Parentheses indicate examples (e.g., preferred) salt or ester forms.

Different classes of bronchodilators target different receptors in the airways. Two commonly used classes are β2-agonists and anticholinergics. β2-Adrenergic agonists (or "132-agonists") act upon the β2-adrenoceptors which induces smooth muscle relaxation, resulting in dilation of the bronchial passages. They tend to be categorised by duration of action. Examples of long-acting β2-agonists (LABAs) include formoterol (fumarate), salmeterol (xinafoate), indacaterol (maleate), bambuterol (hydrochloride), clenbuterol (hydrochloride), olodaterol (hydrochloride), carmoterol (hydrochloride), tulobuterol (hydrochloride) and vilanterol (triphenylacetate). Examples of short-acting β2-agonists (SABA) are albuterol (sulfate) and terbutaline (sulfate).

Typically short-acting bronchodilators provide a rapid relief from acute bronchoconstriction (and are often called "rescue" or "reliever" medicines), whereas long-acting bronchodilators help control and prevent longer-term symptoms. However, some rapid-onset long-acting bronchodilators may be used as rescue medicines, such as formoterol (fumarate). Thus, a rescue medicine provides relief from acute bronchoconstriction. The rescue medicine is taken as-needed/prn (pro re nata). The rescue medicine may also be in the form of a combination product, e.g. ICS-formoterol (fumarate), typically budesonide-formoterol (fumarate) or beclomethasone (dipropionate)-formoterol (fumarate). Thus, the rescue medicine is preferably a SABA or a rapid-acting LABA, more preferably albuterol (sulfate) or formoterol (fumarate), and most preferably albuterol (sulfate).

Anticholinergics (or "antimuscarinics") block the neurotransmitter acetylcholine by selectively blocking its receptor in nerve cells. On topical application, anticholinergics act predominantly on the M3 muscarinic receptors located in the airways to produce smooth muscle relaxation, thus producing a bronchodilatory effect. Examples of long-acting muscarinic antagonists (LAMAs) include tiotropium (bromide), oxitropium (bromide), aclidinium (bromide), umeclidinium (bromide), ipratropium (bromide) glycopyrronium (bromide), oxybutynin (hydrochloride or hydrobromide), tolterodine (tartrate), trospium (chloride), solifenacin (succinate), fesoterodine (fumarate) and darifenacin (hydrobromide).

A number of approaches have been taken in preparing and formulating these medicaments for delivery by inhalation, such as via a dry powder inhaler (DPI), a pressurized metered dose inhaler (pMDI) or a nebulizer.

According to the GINA (Global Initiative for Asthma) Guidelines, a step-wise approach can be taken to the treatment of asthma. At step 1, which represents a mild form of asthma, the patient is given an as needed SABA, such as albuterol sulfate. The patient may also be given an as-needed low-dose ICS-formoterol, or a low-dose ICS whenever the SABA is taken. At step 2, a regular low-dose ICS is given alongside the SABA, or an as-needed low-dose ICS-formoterol. At step 3, a LABA is added. At step 4, the doses are increased and at step 5, further add-on treatments are included such as an anticholinergic or a low-dose oral corticosteroid. Thus, the respective steps may be regarded as treatment regimens, which regimens are each configured according to the degree of acute severity of the respiratory disease.

COPD is a leading cause of death worldwide. It is a heterogeneous long-term disease comprising chronic bronchitis, emphysema and also involving the small airways. The pathological changes occurring in patients with COPD are predominantly localized to the airways, lung parenchyma and pulmonary vasculature. Phenotypically, these changes reduce the healthy ability of the lungs to absorb and expel gases.

Bronchitis is characterized by long-term inflammation of the bronchi. Common symptoms may include wheezing, shortness of breath, cough and expectoration of sputum, all of which are highly uncomfortable and detrimental to the patient's quality of life. Emphysema is also related to long-term bronchial inflammation, wherein the inflammatory response results in a breakdown of lung tissue and progressive narrowing of the airways. In time, the lung tissue loses its natural elasticity and becomes enlarged. As such, the efficacy with which gases are exchanged is reduced and respired air is often trapped within the lung. This results in localised hypoxia, and reduces the volume of oxygen being delivered into the patient's bloodstream, per inhalation. Patients therefore experience shortness of breath and instances of breathing difficulty.

Patients living with COPD experience a variety, if not all, of these symptoms on a daily basis. Their severity will be determined by a range of factors but most commonly will be correlated to the progression of the disease. These symptoms, independent of their severity, are indicative of stable COPD and this disease state is maintained and managed through the administration of a variety drugs. The treatments are variable, but often include inhaled bronchodilators, anticholinergic agents, long-acting and short-acting β2-agonists and corticosteroids. The medicaments are often administered as a single therapy or as combination treatments.

Patients are categorized by the severity of their COPD using categories defined in the GOLD Guidelines (Global Initiative for Chronic Obstructive Lung Disease, Inc.). The categories are labelled A-D and the recommended first choice of treatment varies by category. Patient group A are recommended a short-acting muscarinic antagonist (SAMA) prn or a short-acting β2-aginist (SABA) prn. Patient group B are recommended a long-acting muscarinic antagonist (LAMA) or a long-acting β2-against (LABA). Patient group C are recommended an inhaled corticosteroid (ICS)+a LABA, or a LAMA. Patient group D are recommended an ICS+a LABA and/or a LAMA.

Patients suffering from respiratory diseases like asthma or COPD suffer from periodic exacerbations beyond the baseline day-to-day variations in their condition. An exacerbation is an acute worsening of respiratory symptoms that require additional therapy, i.e. a therapy going beyond their maintenance therapy.

For asthma, the additional therapy for a moderate exacerbation are repeated doses of SABA, oral corticosteroids and/or controlled flow oxygen (the latter of which requires hospitalization). A severe exacerbation adds an anticholinergic (typically ipratropium bromide), nebulized SABA or IV magnesium sulfate.

For COPD, the additional therapy for a moderate exacerbation are repeated doses of SABA, oral corticosteroids and/or antibiotics. A severe exacerbation adds controlled flow oxygen and/or respiratory support (both of which require hospitalization). An exacerbation within the meaning of the present disclosure includes both moderate and severe exacerbations.

FIG. 1 is a front perspective view of an example inhalation device 100. The example, inhalation device 100 may be a breath-actuated inhalation device. The inhalation device 100 may include a top cap 102, a main housing 104, a mouthpiece 106, a mouthpiece cover 108, medicament, and an air vent 125. The top cap 102 may be mechanically attached to the main housing 104. The mouthpiece cover 108 may be hinged to the main housing 104 so that it may open and close to expose the mouthpiece 106. Although illustrated as a hinged connection, the mouthpiece cover 108 may be connected to the inhalation device 100 through other types of connections.

The inhalation device 100 may include a rescue medicament or a maintenance medicament. The rescue medicament may be a SABA or a rapid-onset LABA, such as formoterol (fumarate). The rescue medicament may also be in the form of a combination product, e.g. ICS-formoterol (fumarate), typically budesonide-formoterol (fumarate) or beclomethasone (dipropionate)-formoterol (fumarate). Such an approach is termed "MART" (maintenance and rescue therapy). In some examples, the medicament is albuterol (sulfate), fluticasone (propionate or furoate), or salmeterol (xinafoate) combined with fluticasone (propionate or furoate).

Figure 2:
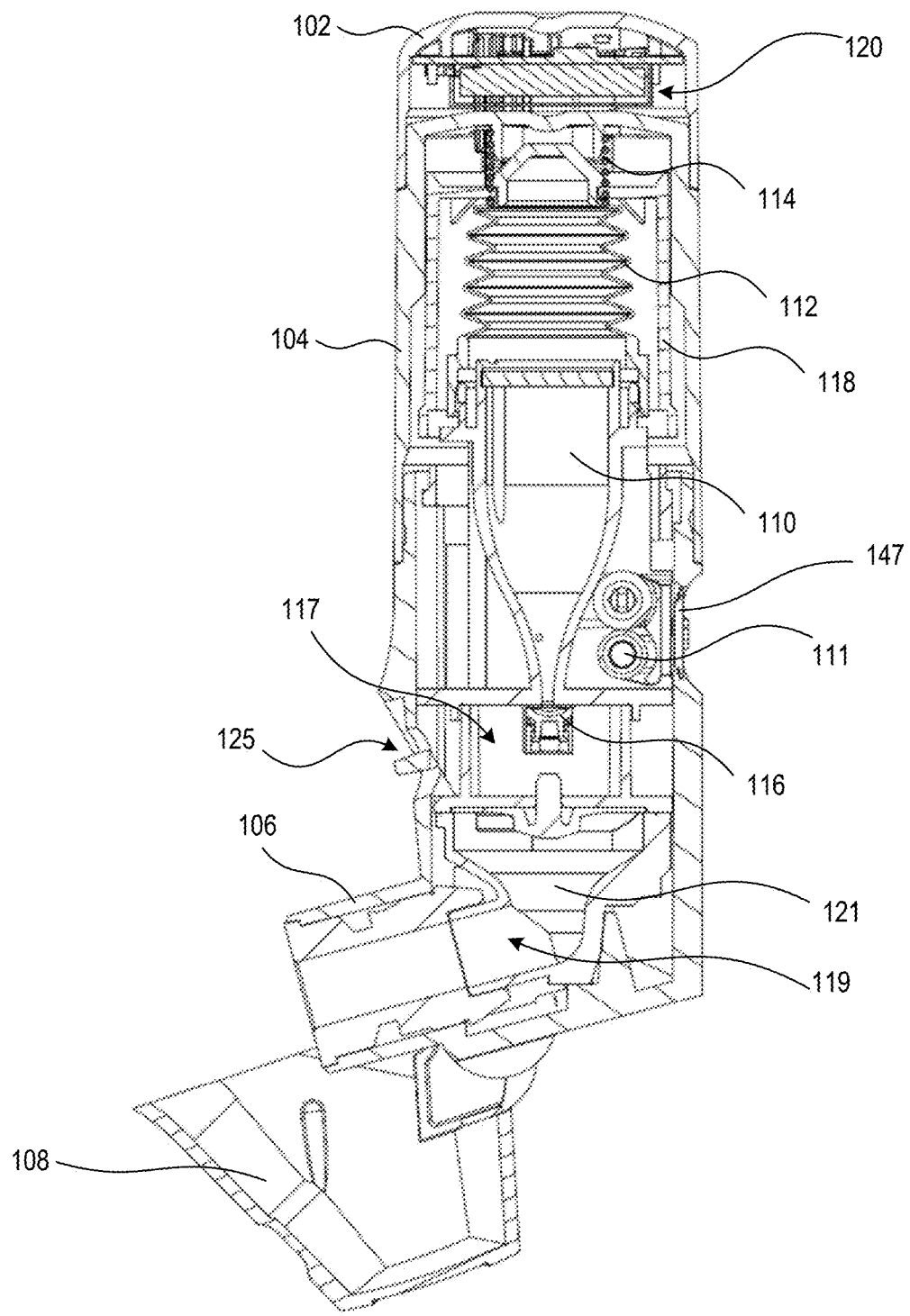
FIG. 2 is a cross-sectional interior perspective view of the example inhalation device.

FIG. 2 is a cross-sectional interior perspective view of the inhalation device 100. Inside the main housing 104, the inhalation device 100 may include a medication reservoir and a dose delivery mechanism/system. For example, the inhalation device may include a medication reservoir 110 (e.g., a hopper), a bellows 112, a bellows spring 114, a yoke 118, a dose counter 111, a transparent window 147, a dosing cup 116, a dosing chamber 117, a deagglomerator 121 and a flow pathway 119. The medication reservoir 110 may include medication, such as dry powder mediation, which may be delivered to the user via the mouthpiece 106. The yoke 118 may be mechanically coupled (e.g., directly or indirectly) with the mouthpiece cover 108 such that a movement of the mouthpiece cover 108 may result in a movement of the yoke 118. For example, when the mouthpiece cover 108 is moved to expose the mouthpiece 106 (e.g., from a closed position to an open position), the yoke 118 may move vertically (e.g., towards or away from the top cap 102) within the inhalation device 100.

The movement of the yoke 118 may cause the bellows 112 to compress, thereby delivering a dose of medication from the medication reservoir 110 to the dosing cup 116. Thereafter, a user may inhale through the mouthpiece 106 to receive the dose of medication. The airflow generated from the user's inhalation may cause the deagglomerator 121 to aerosolize the dose of medication by breaking down the agglomerates of the medication in the dose cup 116. The deagglomerator 121 may be configured to (e.g., fully) aerosolize the medication when the airflow through the flow pathway 119 meets or exceeds a rate or is within a specific range. When aerosolized, the dose of medication may travel from the dosing cup 116, into the dosing chamber 117, through the flow pathway 119, and out of the mouthpiece 106 to the user. If the airflow through the flow pathway 119 does not meet or exceed a rate, or is not within a specific range, all or a portion of the medication may remain in the dosing cup 116. In the event that the medication in the dosing cup 116 has not been aerosolized by the deagglomerator 121, another dose of medication may not be delivered from the medication reservoir 110 when the mouthpiece cover 108 is subsequently opened. Thus, at least a portion of a dose of medication may remain in the dosing cup 116 until the dose has been aerosolized by the deagglomerator 121.

As the user inhales through the mouthpiece 106, air may enter the air vent 125 to provide a flow of air for delivery of the medication to the user. The flow pathway 119 may extend from the dosing chamber 117 to the end of the mouthpiece 106. The flow pathway may include the dosing chamber 117 and the internal portions of the mouthpiece 106. The dosing cup 116 may reside within or adjacent to the dosing chamber 117.

Although illustrated as a combination of the bellows 112, the bellows spring 114, the yoke 118, the dosing cup 116, the dosing chamber 117, and the deagglomerator 121, the dose delivery mechanism may include a subset of the components described and/or the inhalation device 100 may include a different dose delivery mechanism (e.g., based on the type of inhalation device, the type of medication, etc.). For instance, in some examples the medication may be included in a blister strip and the dose delivery mechanism (e.g., one or more wheels, levers, and/or actuators) may be configured to advance the blister strip, open a new blister that includes a dose of medication, and make that dose of medication available to a dosing chamber and/or mouthpiece for inhalation by the user.

In the illustrated example dose delivery mechanism of FIG. 1, the dose counter 111 may be mechanically coupled (e.g., directly or indirectly) with the mouthpiece cover 108 such that the dose counter 111 may increment or decrement when the mouthpiece cover 108 is opened or closed. The dose counter 111 may initially be set to a number of total doses available, which may be the number of doses in the medication reservoir 110 or the number of doses advertised by the manufacturer. As such, the dose counter 111 may be configured to decrease by one each time the mouthpiece cover 108 is moved from the closed position to the open position (or from the open position to the closed position), thereby indicating the remaining number of doses available. Alternatively, the dose counter 111 may initially be set to zero and may be configured to increase by one each time the mouthpiece cover 108 is moved from the closed position to the open position (or from the open position to the closed position), thereby indicating the total number of doses delivered from the medication reservoir 110.

The inhalation device 100 may include an electronics module 120, which may be housed within the top cap 102. The electronics module 120 may include a printed circuit board (PCB) assembly 122 with one or more electrical components, such as a sensor system 128 and a wireless communication circuit 129. The sensor system 128 may be configured to detect one or more parameters associated with the usage of the device and/or the environment in which the device is used or stored. The wireless communication circuit 129 may be configured to transmit the detected parameters to an external device, such as a smartphone, tablet, or computer, for further processing.

Figure 3:
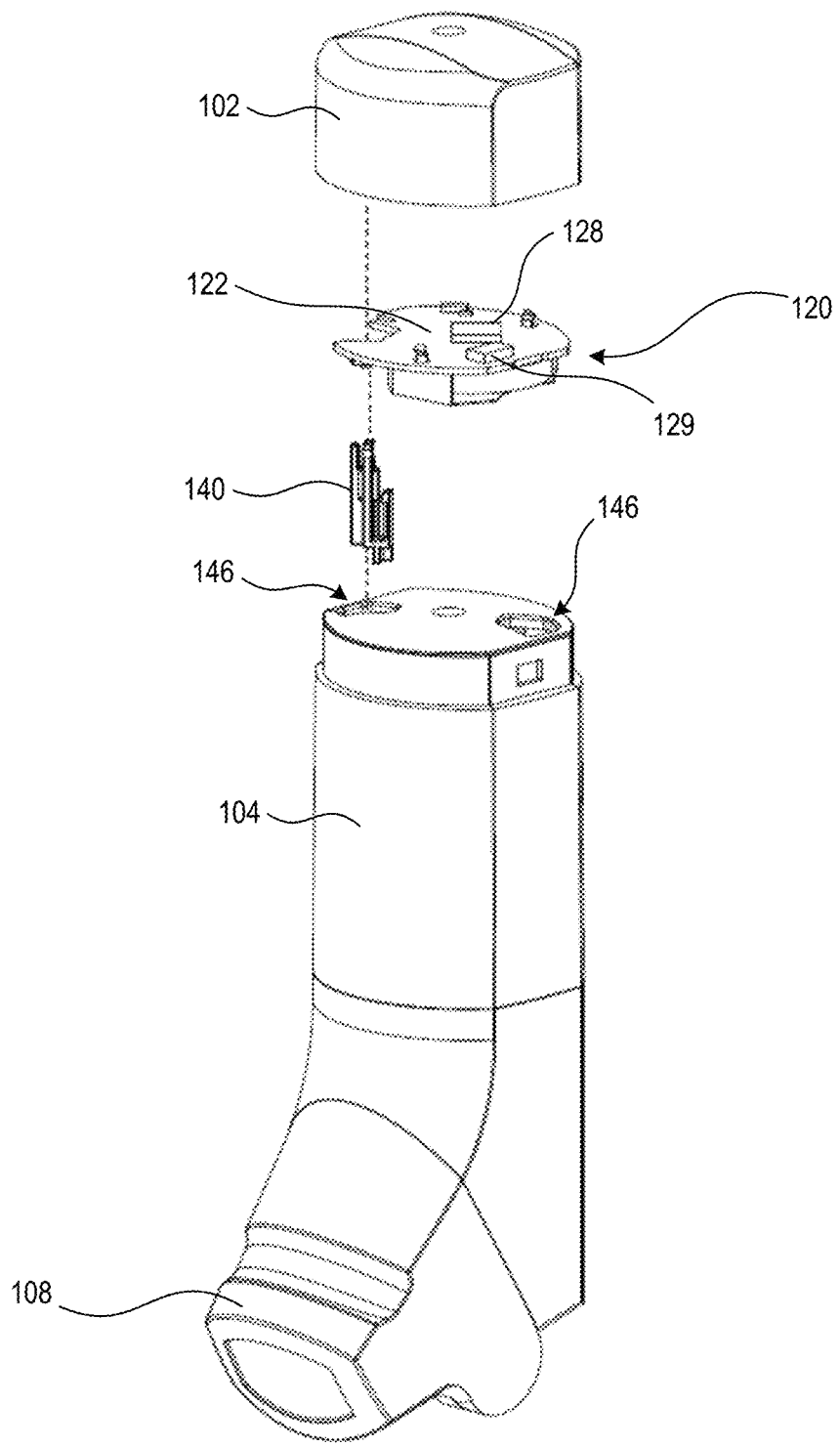
FIG. 3 is an exploded perspective view of the inhalation device with a top cap removed to expose an electronics module.

FIG. 3 is an exploded perspective view of the example inhalation device 100 with the top cap 102 removed to expose the electronics module 120. The top cap 102 may house the electronics module 120, which may include a printed circuit board (PCB) assembly 122. The PCB assembly 122 may include one or more components, such as a sensor system 128 and a wireless communication circuit 129. The top cap 102 may be attached to the main housing 104 via one or more clips (not shown) that engage recesses on the main housing 104. The top cap 102 may overlap a portion of the main housing 104 when connected, for example, such that a substantially pneumatic seal exists between the top cap 102 and the main housing 104. The top surface of the main housing 104 may include one or more (e.g., two) orifices 146. One of the orifices 146 may be configured to accept a slider 140. For example, when the top cap 102 is attached to the main housing 104, the slider 140 may protrude through the top surface of the main housing 104 via one of the orifices 146. The top cap 102 may be removably attached to the main housing 104. Alternatively or additionally, the electronics module 120 may be integrated within the main housing 104 and/or the top cap 102 housing the electronics module 120 may be permanently attached to the main housing 104.

Further, in some examples, the electronics module 120 may reside in a separate device that is outside of and separate from the inhalation device 100. For instance, the electronics module 120 may reside within an add-on device that is configured to be attached to and subsequently removed from the inhalation device 100, for example, when the inhalation device 100 runs out of medication or expires.

In such instances, the user may attached the add-on device that includes the electronics module 120 from one inhalation device 100 to another each time the user receives a new inhalation device 100. The add-on device may be configured to be attached to any component of the inhalation device 100, such as the main housing 104, the mouthpiece, and/or a medication canister housed within the main housing of the main housing 104 of the inhalation device 100 (e.g., such that the sensors are in fluid communication with the mouthpiece and/or flow channel of inhalation device 100. As such, in some examples, the inhalation device 100 may be replaced by an add-on device that includes the electronics module 120 (e.g. in whole or in part), and possibly an inhaler that does not include electronics.

Figure 4:
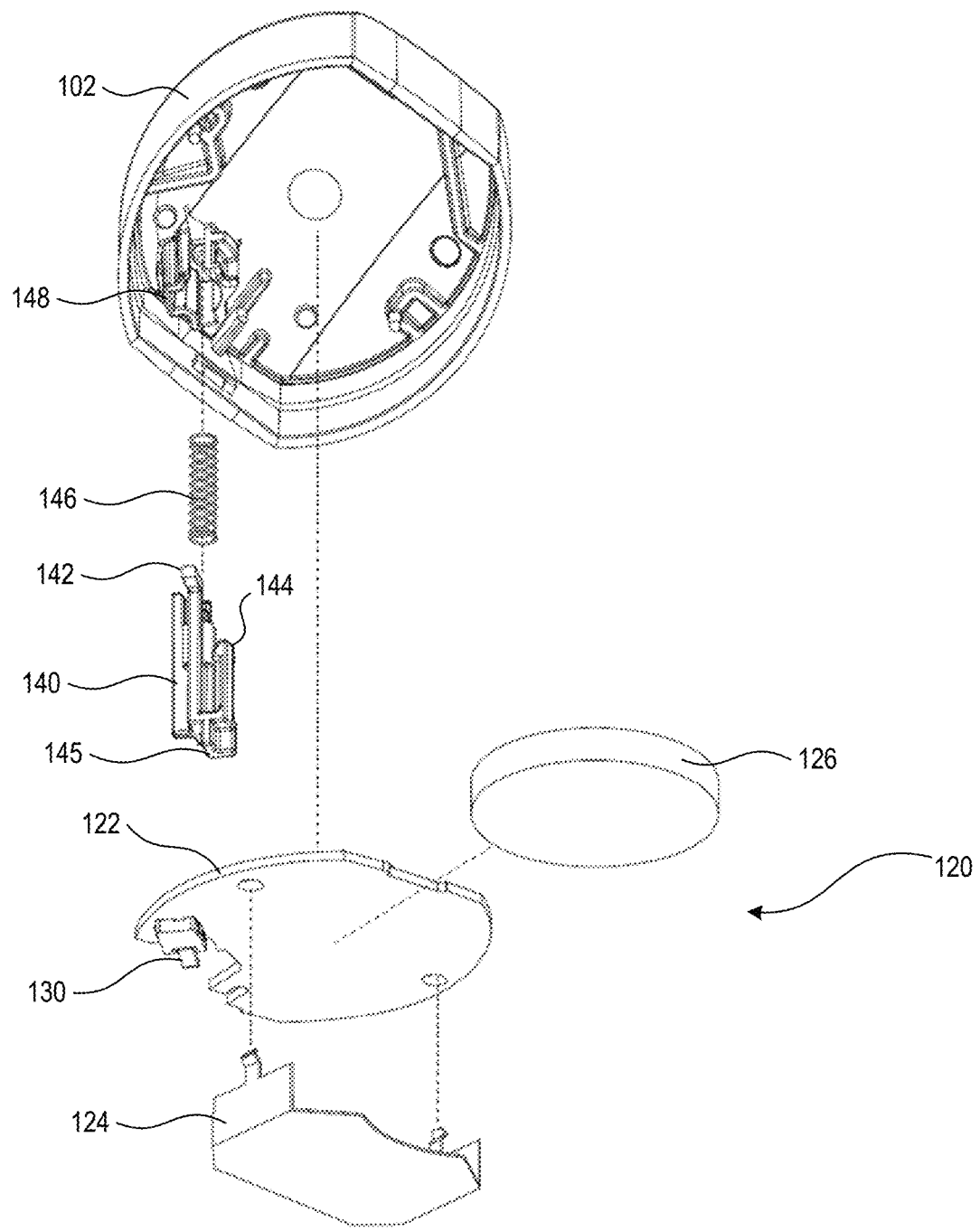
FIG. 4 is an exploded perspective view of the top cap and the electronics module of the inhalation device.

FIG. 4 is an exploded perspective view of the top cap 102 and the electronics module 120. As shown in FIG. 4, the slider 140 may define an arm 142, a stopper 144, and a distal base 145. The distal end 145 may be a bottom portion of the slider 140. The distal end 145 of the slider 140 may be configured to abut the yoke 118 that resides within the main housing 104. The top cap 102 may include a slider guide 148 that is configured to receive a slider spring 146 and the slider 140. The slider spring 146 may reside within the slider guide 148. The slider spring 146 may engage an inner surface of the top cap 102, and the slider spring 146 may engage (e.g., abut) an upper portion (e.g., a proximate end) of the slider 140. When the slider 140 is installed within the slider guide 148, the slider spring 146 may be partially compressed between the top of the slider 140 and the inner surface of the top cap 102. For example, the slider spring 146 may be configured such that the distal end 145 of the slider 140 remains in contact with the yoke 118 when the mouthpiece cover 108 is closed.

The distal end 145 of the slider 145 may also remain in contact with the yoke 118 while the mouthpiece cover 108 is opened or closed. The stopper 144 of the slider 140 may engage a stopper of the slider guide 148, for example, such that the slider 140 is retained within the slider guide 148 through the opening and closing of the mouthpiece cover 108, and vice versa. The stopper 144 and the slider guide 148 may be configured to limit the vertical (e.g., axial) travel of the slider 140. This limit may be less than the vertical travel of the yoke 118. Thus, as the mouthpiece cover 108 is moved to an open position, the yoke 118 may continue to move in a vertical direction towards the mouthpiece 106 but the stopper 144 may stop the vertical travel of the slider 140 such that the distal end 145 of the slider 140 may no longer be in contact with the yoke 118.

As noted above, the electronics module 120 may include one or more components, such as the sensor system 128 and the wireless communication circuit 129. The electronics module 120 may further include a switch 130, a power supply 126 (e.g., a battery), a power supply holder 124, an indicator (e.g., a light emitting diode (LED)), a controller (e.g., processor) and/or memory. When used herein, the terms controller and processor may be used interchangeably. One or more of the components of the electronics module 120 may be mounted on, and electrically coupled to, the PCB 122. The controller and/or memory may be physically distinct components of the PCB 122. Alternatively, the controller and memory may be part of a chipset mounted on the PCB 122. For example, the wireless communication circuit 129 may include the controller and/or memory for the electronics module 120. The controller of the electronics module 120 may include a microcontroller, a programmable logic device (PLD), a microprocessor, an application specific integrated circuit (ASIC), a field-programmable gate array (FPGA), or any suitable processing device or control circuit. The memory may include computer-executable instructions that, when executed by the controller, cause the controller to implement the processes of the electronics module as described herein.

The controller may access information from, and store data in the memory. The memory may include any type of suitable memory, such as non-removable memory and/or removable memory. The non-removable memory may include random-access memory (RAM), read-only memory (ROM), a hard disk, or any other type of memory storage device. The removable memory may include a subscriber identity module (SIM) card, a memory stick, a secure digital (SD) memory card, and the like. The memory may be internal to the controller. The controller may also access data from, and store data in, memory that is not physically located within the electronics module 120, such as on a server or a smartphone.

The battery 126 may provide power to the components of the PCB 122. The battery 126 may be any suitable source for powering the electronics module 120, such as a coin cell battery, for example. The battery 126 may be rechargeable or non-rechargeable. The battery 126 may be housed by the battery holder 124. The battery holder 124 may be secured to the PCB 122 such that the battery 126 maintains continuous contact with the PCB 122 and/or is in electrical connection with the components of the PCB 122. The battery 126 may have a battery capacity that may affect the life of the battery 126. As will be further discussed below, the distribution of power from the battery 126 to the one or more components of the PCB 122 may be managed to ensure the battery 126 can power the electronics module 120 over the useful life of the inhalation device 100 and/or the medication contained therein.

The switch 130 may be actuated by the dose delivery mechanism of the inhalation device 100. When incorporated using the example dose delivery mechanism described herein, the switch 130 may be actuated by a slider 140 as the mouthpiece cover 108 is moved from a closed position to an open position. Although it should be appreciated that if the inhalation device 100 includes a different dose delivery mechanism, then the switch 130 may be actuated by a different component of the dose deliver mechanism. When the switch 130 is actuated, the electronics module 120 may generate a signal causing the electronics module 120 to change states, such as from an off or sleep state to an active state. When in the active state, the controller of the electronics module 120 may wake and provide power to the sensor system 128 to enable the sensor system 128 to take measurement readings. Further, the electronics module 120 may store a dosing event (e.g., which may be referred to as a dose delivery event or an actuation event) each time the switch 130 is actuated. As described in more detail below, the electronics module 120 may have a plurality of power states, each with respective power consumption levels. For example, the electronics module 120 may be configured to operate in a system off state, a sleep state, and/or an active state, where the electronics module 120 consumes the least amount of power while in the off state (e.g., no power or just enough to run a clock), the sleep state uses more power than the off state (e.g., to drive the memory, the communication circuit, and/or a timer or clock), and the active state uses the most amount of power (e.g., to drive the controller, one or more sensors, the communication circuit, potentially in a faster advertising mode than the sleep state, and/or a timer or clock).

The sensor system 128 may include one or more sensors, such as one or more pressure sensors, temperature sensors, humidity sensors, orientation sensors, acoustic sensors, and/or optical sensors. The pressure sensor(s) may include a barometric pressure sensor (e.g., an atmospheric pressure sensor), a differential pressure sensor, an absolute pressure sensor, and/or the like. The sensors may employ microelectromechanical systems (MEMS) and/or nanoelectromechanical systems (NEMS) technology. The pressure sensor(s) may be configured to detect and/or measure pressure changes within the inhalation device 100 caused by an inhalation from (or an exhalation into) the mouthpiece 106. One or more of the measured pressure changes may be used to determine the amount of airflow (e.g., an airflow rate) through the flow pathway 119 of the mouthpiece 106. The magnitude of the airflow may indicate whether a user is properly using the device 100. For example, if the deagglomerator 121 is configured to aerosolize a dose of medication when the airflow rate exceeds a threshold, a use may be deemed compliant if the determined airflow rate is above the threshold. Conversely, the use may be deemed non-compliant if the determined airflow is below the threshold.

The electronics module 120 (e.g., and/or a mobile application residing on an external device) may use measurements from the sensor system 128 to determine one or more dosing events. For example, the electronics module 120 may be configured to compare one or more measurements from the sensor system 128 to one or more threshold values to categorize an inhalation event as a no/low inhalation event, a fair inhalation event, a good inhalation event, an excessive inhalation event, and/or an exhalation event. For example, the electronics module may generate a good inhalation event when the measurements from the sensor system 128 indicate a flow rate in a particular range (e.g., between 200 liters per min (L/min) and 45 L/min), generate a fair inhalation event when the measurements from the sensor system 128 indicate a flow rate in another range (e.g., 30 L/min and 45 L/min), generate a no inhalation event when the measurements from the sensor system 128 indicate a flow rate that is less than a threshold value (e.g., 30 L/min), and an excessive inhalation event when the measurements from the sensor system 128 indicate a flow rate that is greater than an upper threshold (e.g., greater than 200 L/min).

The temperature sensor(s) may include a thermistor, a thermocouple, a resistance temperature detector, a temperature sensor chip and the like. The temperature sensor(s) may be configured to provide a temperature reading to the controller of the electronics module 120 and/or aggregated temperature readings over time. The temperature sensor(s) may be configured to measure the external temperature in the space proximate to the inhalation device 100. Accordingly, main housing 104 and/or the top cap 102 may include an opening (e.g., a vent) to allow for the temperature sensor(s) to measure the ambient temperature external to the housing.

Alternatively or additionally, the temperature sensor(s) may be configured to measure temperature within the inhalation device 100, such as within one or more of the top cap 102, the main housing 104, and/or the mouthpiece 106 of the inhalation device 100. The ability to measure both internal and external temperature may allow the electronics module 120 to determine the operating temperature of the components of the electronics module 120, the temperature of the air flowing through the inhalation device 100 when a user inhales through the inhalation device 100, etc. Accordingly, the electronics module 120 may be configured to detect an over or under temperature condition, such as an over temperature condition of one or more of the components of the electronic module 120 (e.g., such as another sensor, like a pressure sensor), an over temperature condition of the inhalation device 100, an ambient temperature that exceeds a threshold, etc. The electronics module 120 may be configured to cause the communication circuit 129 to transmit a temperature message to an external device (e.g., a mobile device) that indicates an over temperature condition, an ambient temperature reading, and/or a temperature reading of internal to the inhalation device 100 (e.g., such as a temperature change detected through the flow channel of the inhalation device 100).

Further, in some examples, the pressure sensor may include a temperature sensor. The humidity sensor(s) may include a capacitive sensor, a resistive sensor, a thermal conductivity sensor and the like. The humidity sensor(s) may be configured to provide a humidity reading to the controller of the electronics module 120 and/or aggregated humidity readings over time. The temperature and/or humidity measurements may be used to identify and track the environmental conditions in which the inhalation device 100 is used or stored. The temperature and/or humidity measurements may be used to determine whether the device 100 is being operated or stored in an environment that could compromise the proper operation of the device 100 and/or the efficacy of the medication in the medication reservoir 110. For example, extreme hot or cold temperatures, or excessive humidity levels, may contribute to device failures and/or alter the properties of the medication in the reservoir 110.

The orientation sensor(s) may include an accelerometer, a gravity (G) sensor, a gyroscope, a magnetometer and the like. The orientation sensor(s) may be configured to provide an orientation reading (e.g., acceleration, rotation, direction, etc.) to the controller of the electronics module 120 and/or aggregated orientation readings over time. The data from the orientation sensor(s) may be used to identify and track how a user is handling or interacting with the device 100 when attempting to receive a dose of medication. The data may be used to determine whether the device 100 is being operated in a compliant manner, such as during dose delivery. For example, the orientation sensor(s) may indicate whether a user is holding the device 100 upside down during inhalation, which may prevent or impede the delivery of a full dose of medication from the dosing cup 116 and/or the dosing chamber 117.

As noted above, the electronics module 120 may include one or more indicators, such as an LED, which may be housed or located on the device 100 such that any provided feedback may be observed by a user. The controller in the electronics module 120 may operate the indicators to provide feedback to users regarding their use of the inhalation device 100 and/or the conditions under which the inhalation device 100 is being used or stored. The controller may cause the status of the indicators to change (e.g., the LED may turn on, flash, change color, etc.) if one or more measurements from the sensor system 128 are above or below a predetermined threshold. For example, the controller may cause the LED may illuminate if the measured change in pressure, the determined airflow rate, the measured temperature and/or the measured humidity level exceeds the threshold. The controller may cause the LED may illuminate if the data from the orientation sensor(s) indicates that the device 100 is not being held properly.

The data from the sensor system 128 (e.g., pressure change, temperature, humidity level, etc.) and/or parameters derived therefrom (e.g., airflow rate) may be communicated to an external device, such as a smartphone, tablet or computer. More specifically, the wireless communication circuit 129 in the electronics module 120 may include a transmitter and/or receiver (e.g., a transceiver), as well as additional circuitry. For example, the wireless communication circuit 129 may include a Bluetooth chip set (e.g., a Bluetooth Low Energy chip set), a ZigBee chipset, a Thread chipset, etc. As such, the electronics module 120 may wirelessly provide data to the external device for review and/or additional processing. The external device may include software for processing the received information and for providing compliance and adherence feedback to users of the inhalation device 100 via a graphical user interface (GUI).

The power supply 126 may provide power to the electrical components of the PCB 122. The power supply 126 may be any suitable source for powering the electronics module 120, such as a coin cell battery, for example. The power supply 126 may be rechargeable or non-rechargeable. The power supply 126 may be housed by the power supply holder 124. The power supply holder 124 may be secured to the PCB 122 such that the power supply 126 maintains continuous contact with the PCB 122 and/or is in electrical connection with the components of the PCB 122.

The selection of the power supply 126 may be based various factors, such as its size, weight, cost and/or power capacity. Basing the selection of the power supply 126 on one attribute may negatively affect the operation or design of the inhalation device 100 with regard to other attributes of the power supply 126. For example, a supply with the smallest physical dimensions, lowest weight, and/or lowest cost may have insufficient capacity to power the electronics module 120 for a desired period (e.g., the normal operating life of the device 100). Conversely, a supply with sufficient capacity to power the electronics module 120 for the desired period may not fit within the space available in the top cap 102 and/or may be more expensive. Accordingly, the selection of the power supply 126 may include balancing one or more of its technical and/or commercial attributes. In addition, the operation of the electronics module 120 may be configured to limit or manage the power consumption from the power supply 126, which may enable the selection of a smaller, less expensive supply that can reliably power the electronics module 120 for the desired period and under the desired operating conditions.

The electronics module 120 may have a plurality of power states, each with respective power consumption levels. For example, the electronics module 120 may be configured to operate in a system off state, a sleep state, and/or an active state. While the electronics module 120 is in the active state, the electronics module 120 may operate in one or more modes, such as a measurement mode, a data storage/data processing mode, an advertising mode, and/or a connected mode. It will be appreciated that the electronics module 120 may operate in multiple modes at one time (e.g., the modes may overlap).

In the measurement mode, the controller of the electronics module 120 may power on the sensor system 128. The controller may cause the sensor system 128 to take pressure measurement readings, temperature readings, humidity readings, orientation readings, etc. for a predetermined period (e.g., up to 60 seconds) and/or until the mouthpiece cover 108 is closed or no changes in measurements are detected. The controller may turn off one or more components of the electronics module 120 while the sensor system 128 is capturing readings to further conserve power. The sensor system 128 may sample the readings at any suitable rate. For example, the sensor system 128 may have a sample rate of 100 Hz and thus a cycle time of 10 milliseconds. The sensor system 128 may generate a measurement complete interrupt after the measurement cycle is complete. The interrupt may wake the controller or cause it to turn on one or more components of the electronics module 120. For example, after or while the sensor system 128 is sampling one or more pressure measurements, temperature readings, humidity readings, orientation readings, etc., the controller may process and/or store the data and, if measurements are complete, power off the sensor system 128.

In the data storage/data processing mode, the controller may power on at least a portion of the memory within the electronics module 120. The controller may process the readings from the sensor system 128 to compute, estimate, or otherwise parameters (e.g., usage and/or storage conditions) and store the parameters in memory. The controller may also compare the readings and/or parameters to one or more thresholds or ranges to assess how the inhalation device 100 is being used and/or the conditions under which the device 100 is being used. Depending on the results of the comparison, the controller may drive the indicators (e.g., an LED) to provide feedback to the user of the inhalation device 100. As noted above, the electronics module 120 may operate in the measurement mode and the data storage/data processing mode simultaneously.

In the connected mode, the communication circuit and memory may be powered on and the electronics module 120 may be connected to or "paired" with an external device, such as a smartphone. The controller may retrieve data from the memory (e.g., sensor data and/or parameters derived from the sensor data) and wirelessly transmit the data to the external device. The controller may retrieve and transmit all of the data currently stored in the memory. The controller may also retrieve and transmit a portion of the data currently stored in the memory. For example, the controller may be able to determine which portions have already been transmitted to the external device and then transmit the portion(s) that have not been previously transmitted. Additionally or alternatively, the external device may request specific data from the controller, such as any data that has been collected by the electronics module 120 after a particular time or after the last transmission to the external device. The controller may retrieve the specific data, if any, from the memory and transmit the specific data to the external device.

Further, when connected with the external device, the electronics module 120 may be configured to transmit Bluetooth special interest group (SIG) characteristics for managing access to data stored in the module 120. The Bluetooth SIG characteristics may include one or more of a manufacturer name of the inhalation device 100, a serial number of the inhalation device 100, a hardware revision number of the inhalation device 100, and/or a software revision number of the inhalation device 100. When connected with the external device, the electronics module 120 may retrieve data from memory and transmit the data to the external device.

The data stored in the memory of the electronics module 120 (e.g., the signals generated by the switch 130, the measurement readings taken by the sensor system 128 and/or the parameters computed by the controller of the electronics module 120) may be transmitted to an external device, which may process and/or analyze the data to determine the usage parameters associated with the inhalation device 100. The data may include any a usage parameter (e.g., usage event), which for example, may include or indicate a use of the respective inhaler. In a relatively simple implementation, the at least one value may comprise "TRUE" when use of, for example an inhalation using, the respective inhaler has been determined, or "FALSE" when no such use of the respective inhaler is determined. However, the usage parameters may include any combination of the events described herein, such as, no inhalation events, low inhalations events, good inhalation events, excessive inhalation events, exhalation events, actuation events, error events, underuse events, overuse events, etc. Further, the usage parameters may include a count of the number of uses of the inhalation device 100, a measure of airflow of inhalation device 100, other measurements indicating the usage of the medicament of inhalation device 100, such as the actuation of a switch configured to detect usage of inhalation device 100 (e.g., when the mouthpiece cover is moved from a closed position to an open position and/or a switch that is actuated upon the priming of the inhaler, such as to move and/or open a blister of medicament comprised within the inhaler), feedback from one or more sensors configured to detect use of inhalation device 100, and/or the actuation of one or more buttons configured to be depressed upon use of inhalation device 100.

Further, it should be appreciated that the electronics module (e.g., the processor) 120 is configured to timestamp the data (e.g., associate a timestamp with the data). For example, the electronics module 120 may include a local mean time clock, and may associate a timestamp that indicates the local mean time of the inhalation device 100 with the data determined by the inhalation device 100. In other examples, the electronics module 120 may operate as an internal counter. When operating as an internal counter, the electronics module 120 determines a relative count (e.g., as opposed to providing a mean solar time, such as a local mean time), and associates the relative count with the determined data. For instance, the electronics module 120 may start an internal counter (e.g., which counts up from 0 indefinitely) when, for example, the electronics module 120 is woken out of an energy-saving sleep mode for the first time (e.g., after the mouthpiece cover is opened for the first time). Thereafter, any timestamp generated by the electronics module 120 may be a relative time (or count) based on the internal counter. The electronics module 120 may periodically update the system clock every 250 microseconds (μs).

Further, a software application residing on the external device may generate feedback for the user based on data received from the electronics module 120. For example, the software application may generate daily, weekly, or monthly report, provide confirmation of error events or notifications, provide instructive feedback to the user, and/or the like.

Figure 5:
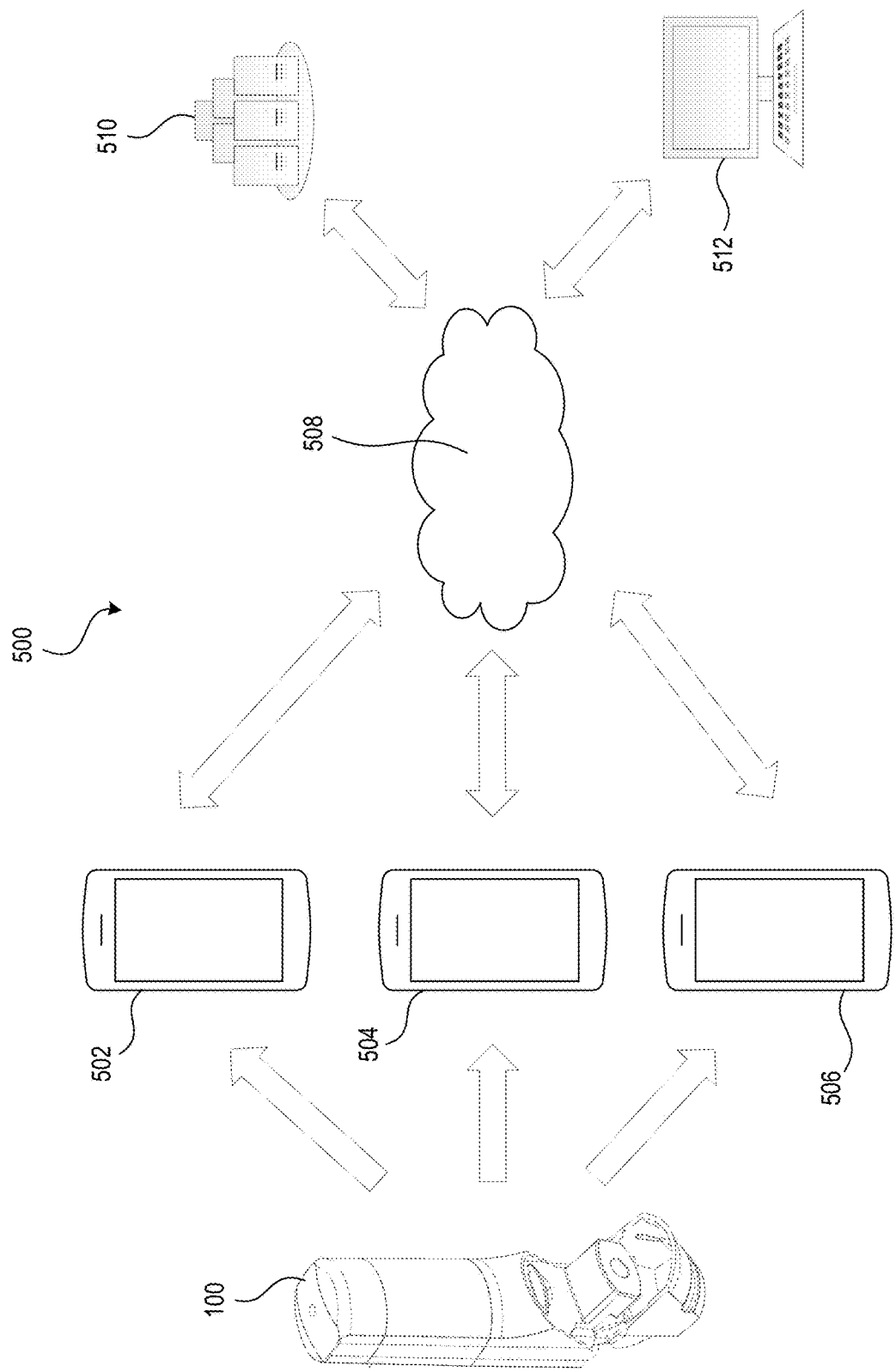
FIG. 5 is a diagram of an example system including the inhalation device.

FIG. 5 is a diagram of an example system 500 including the inhalation device 100, mobile devices 502, 504, 506, a public and/or private network 508 (e.g., any combination of the Internet, a cloud network, and/or the like), and a computer (e.g., a server) 512 associated with a health care provider, such as a hospital or hospital system, a health system, a medical group, a physician, a clinic, and/or a pharmaceutical company. The system 500 also includes a digital health platform (DHP) 510 that resides on one or more servers, and may include computer software configured to perform the functions described in relation to the DHP 510.

The mobile devices 502, 504, 506 may include a smart phone (e.g., an iPhone® smart phone, an Android® smart phone, or a Blackberry® smart phone), a personal computer, a laptop, a wireless-capable media device (e.g., MP3 player, gaming device, television, a media streaming devices (e.g., the Amazon Fire TV, Nexus Player, etc.), etc.), a tablet device (e.g., an iPad® hand-held computing device), a Wi-Fi or wireless-communication-capable television, a wearable device (e.g., the Apple Watch®), or any other suitable Internet-Protocol-enabled device. The mobile devices 502, 504, 506 may include a processor, memory, a communication circuit (e.g., a transceiver), speakers, microphone, and/or a display screen. The mobile devices 502, 504, 506 may have stored thereon a mobile application that is configured to cause the mobile device to perform the functions described herein, such as communicate with one or more inhalation devices 100 and/or the DHP 510, receive, process, and/or aggregate the data received from the inhalers, generate new data and/or alerts based on the data received from the inhalers, and/or generate feedback (e.g., alerts), such as notifications, GUIs, or audio feedback, based on the inhaler data.

Also provided is a computer program comprising computer program code which is adapted, when the computer program is run on a computer, to implement any of the methods and technique described herein. In a preferred embodiment, the computer program takes the form of the mobile application, at least partially, for example the mobile application residing on a mobile device. And in some examples, the computer program is provided partially as the mobile application and partially as the DHP 510. The embodiments described herein for the system 500 are applicable to the method and the computer program. Moreover, the embodiments described for the method and computer program are applicable to the system 500.

Although described as mobile devices, the system 500 may, in some examples, include a stationary devices or a combination of mobile devices and stationary devices. The stationary devices include smart home interface devices, such as smart speakers, smart displays, smart home automation devices, and/or the like. The stationary devices include similar hardware and/or software as the mobile devices described herein (e.g., a processor, memory, a communication circuit (e.g., a transceiver), speakers, microphone, and/or a display screen), and therefore, are configured to perform the functions described herein with respect to the mobile devices.

The mobile devices 502, 504, 506 may be configured to communicate with the inhalation device 100. The mobile devices 502, 504, 506 may also be configured to communicate with the public and/or private network 508, which may be in communication with the DHP 510 and/or a computer associated with a health care provider 512. For example, the mobile devices 502, 504, 506 may include communication circuit (e.g., a transceiver), and as such may be configured to transmit and/or receive RF signals via a Wi-Fi communication link, a Wi-MAX communications link, a Bluetooth® or Bluetooth Smart communications link, a near field communication (NFC) link, a cellular communications link, a television white space (TVWS) communication link, or any combination thereof. The mobile devices 502, 504, 506 may transfer data through the public and/or private network 508 to the DHP 510 using, for example, a dedicated API. For example, the mobile devices 502, 504, 506 may send usage data relating to one or more inhalation devices 100 to the DHP 510.

As noted above, the inhalation device 100 may include the communication circuit 129, such as a Bluetooth radio, for transferring data to an external device (e.g., one or more of the mobile devices 502, 504, 506). The data may be referred to as usage data, usage parameters, and/or usage events. The data may include any of the data described herein, such as the signals generated by the switch 130, the measurement readings taken by the sensor system 128 and/or parameters computed by the controller of the electronics module 120. The data may include any combination of no inhalation events, low inhalations events, good inhalation events, excessive inhalation events, exhalation events, actuation events, error events, underuse events, overuse events, etc. The data may include a count of the number of uses of the inhalation device 100, a measure of airflow of inhalation device 100, other measurements indicating the usage of the medicament of inhalation device 100, such as the actuation of a switch configured to detect usage of inhalation device 100 (e.g., when the mouthpiece cover is moved from a closed position to an open position and/or a switch that is actuated upon the priming of the inhaler, such as to move and/or open a blister of medicament comprised within the inhaler), feedback from one or more sensors configured to detect use of inhalation device 100, and/or the actuation of one or more buttons configured to be depressed upon use of inhalation device 100. The data may be associated with a timestamp, for example, as described herein.

The inhalation device 100 may receive data from the mobile devices 502, 504, 506, such as, for example, program instructions, operating system changes, dosage information, alerts or notifications, acknowledgments, etc. Further, although illustrated as a single inhalation device 100, the system 500 may include any number of inhalation devices 100 that are associated with a plurality of different users. It should be noted that some users will have multiple inhalation devices 100 that include the same medicament. For example, a user may have multiple inhalation devices 100 that include a rescue medicament (e.g., and keep them at different locations). Further, a user may have multiple inhalation devices 100 that include a particular maintenance medicament, such as when they are transitioning between refills. Further the system 500 is configurable with the inhalation devices 100 of a plurality of different users. As such, the system 500 is configured to communication, via respective mobile devices, with a plurality of different inhalers that are associated with a plurality of different users.

The mobile devices 502, 504, 506 may process and analyze the data to determine the usage parameters associated with the inhalation device 100. For example, the mobile devices 502, 504, 506 may process the data to identify usage events, such as no inhalation events, low inhalations events, good inhalation events, excessive inhalation events, exhalation events, actuation events, error events, underuse events, overuse events, etc. The mobile devices 502, 504, 506 include a display device and software for visually presenting the usage parameters and/or data related to usage events through a GUI on the display device.

The mobile devices 502, 504, 506 may be configured to receive data (e.g., usage events) and associated timestamps (e.g., a relative count from an internal counter of the electronics module 120) from the inhalation device 100. The mobile devices 502, 504, 506 may determine a local mean time and a time zone for a timestamp, and associate the local mean time and time zone with the data (e.g., usage event). The mobile devices 502, 504, 506 may then send the data and the associated local mean time and time zone to the DHP. The DHP may associated the data, local mean time, and time zone with a user. Alternatively or additionally, the mobile devices 502, 504, 506 may associate the data, local mean time, and time zone with a user, and/or the DHP may determine the local mean time based on the timestamp received from the inhalation device 100.

The DHP is configured to receive and aggregate inhaler data (e.g., usage events) from inhalers that are associated with a plurality of different users. In some examples, the DHP may reside on or across one or more servers, and may include computer software configured to perform the functions described in relation to the DHP. For example, the DHP may include a dashboard application that may be accessible by the computer 512 associated with a health care provider, such as a hospital or hospital system, a health system, a medical group, a physician, a clinic, and/or a pharmaceutical company. In some examples, the dashboard application is a web application (e.g., a web portal). For example, the DHP is also configured to provide data, such as inhaler data, to clinicians and physicians through the use of the dashboard application (e.g., via a REST API).

The DHP 510 is configured to receive and aggregate data from inhalation devices 100, where the inhalers may be associated with a plurality of different users. For example, the DHP 510 is configured to receive and store inhaler data from the mobile devices 502, 504, 506 (e.g., the patient-facing mobile applications). The inhaler data may include any of the data described with reference to the inhalers described herein, such as usage events, error events, inhalation profiles, associated timestamps, medicament types, etc. The DHP 510 is configured to analyze and manipulate the data. For example, the DHP 510 may aggregate the data across of the inhalation devices that it receives data from, and then the DHP 510 may analyze the aggregated data, for example, to determine one or more metrics, provide feedback, etc. Further, the DHP 510 is also configured to provide data (e.g., or analytical information based on the data) to the user (e.g., via mobile devices 502, 504, 506) or to the computer 512 associated with a health care provider (e.g., via the dashboard application). The inhaler data may include any of the data described with reference to the inhalers described herein.

The inhaler data may be associated with an inhalation device 100 and/or a user profile, for example, at the mobile devices 502, 504, 506 and/or at the DHP 510. One user profile may be associated with multiple inhalation devices 100 of the same and/or different medicament types. The DHP 510 may also de-identify (e.g., disassociate) the inhaler data with a particular user profile, and the DHP 510 may perform analytics on de-identified data relating to the inhalation devices 100. Although described as receiving the inhaler data from the mobile devices 502, 504, 506, in some examples, the DHP 510 may receive the data directly from the inhalation devices 100 themselves, such as in instances where the communication circuits of the inhalation devices 100 include cellular chipsets that are capable of communicating directly with the DHP 510.

Each time data is transferred from the inhalation device 100 to an external device, such as a one or more of the mobile devices 502, 504, 506, the power supply 126 may provide power to one or more electrical components in the electronics module 120, such as the communications circuit 129. As such, the frequency of data transfers from the inhalation device 100 may affect overall power consumption and the ability of the power supply 126 to power the electronics module 120 for the desired period. That is, more frequent data transfers to an external device and/or data transfers to multiple external devices may increase the power requirements of the electronics module 120 and decrease the functional life of the power supply 126. Accordingly, the system 500 may be configured to limit the number of times that the inhalation device 100 transmits new data to an external device (e.g., limit the transmission to a single data transfer). Further, in some examples, the inhalation device 100 may be prevented from transmitting data more than a limited number of times (e.g., more than once). After the data is transferred from the inhalation device 100 to an external device, the DHP 510 may be configured to receive the data from the mobile device, and transmit the data to the other authorized mobile device(s) associated with the user and the medicament within the system 500. Further, in some examples, the mobile device (e.g., a mobile application residing on an external device) may check the system 500 (e.g., the DHP 510) for information before requesting data from the inhalation device 100, for example, to limit energy use of the inhalation device 100. For instance, in some examples, when the mobile device and an inhalation device enter a connected mode, the mobile device may first request new data relating to the inhalation device 100 from the DHP 510 (e.g., as described herein) prior to requesting data from the inhalation device 100. As such, the mobile device ensures that it has the most updated data that the inhalation device 100 has transmitted prior to requesting new data from the inhalation device 100.

In one example, the inhalation device 100 may be provided to a child who is asthmatic. The child may have the mobile device 502 and the child's parents may have the mobile devices 504, 506. Each of the mobile devices 502, 504, 506 may include a mobile application that is configured to process and/or display data collected from the inhalation device 100. The mobile applications on the mobile devices 504, 506 may enable the child's parents to monitor the conditions or parameters associated with their child's use of the inhalation device 100. The mobile application on the mobile device 502 may enable the child to do the same. As such, data from the inhalation device 100 may need to be transferred to three separate external devices.

If the data is transferred directly from the inhalation device 100 to the mobile devices 502, 504, 506, the power consumption related to wireless transmissions may increase (e.g., increase three-fold) when compared to communicating with a single external device. This increase in power consumption may cause the functional life of the power supply 126 to be less than the expected life of the inhalation device 100 (e.g., less than the time during which the user is expected to receive doses of medication from the inhalation device 100). Accordingly, to extend the life of the power supply 126, one or more of the electronics module 120, a mobile application residing on the mobile device 504, and/or a DHP 510 may be configured to limit the number of times the data can be transferred from the electronics module 120 to an external device (e.g., limited to a single transfer of the data from the inhalation device 100).

For example, referring again to FIG. 5, a child may be prescribed a medication that can be administered via the inhalation device 100. The child's mother may download a mobile application on her mobile device, such as the mobile device 504. The mobile application may enable the mobile device 504 to wirelessly connect with the inhalation device 100 and to receive data collected by the electronics module 120. Such data may be indicative of when doses were delivered from the device 100. The mobile application may also store the child's prescribed dosing regimen. As such, the mobile application may enable the child's mother to monitor when and how often her child is using the inhalation device 100 and whether her child is adhering to the dosing regimen. The child and the child's father may similarly download the mobile application for their respective mobile devices 502, 506. However, to extend the life of the power supply 126 of the electronics module 120, the system 500 may be configured to limit the transfer of data from the electronics module 120 to a single transfer of the data (e.g., a transfer of the data to just one of the mobile devices 502, 504, 506).

For example, in some embodiments, when a mobile device, such as the mobile device 504, is within communication range of the electronics module 120 of the inhalation device 100, the mobile device 504 (e.g., the mobile application residing thereon) may transmit a request for data from the inhalation device 100. The request may include an indication of the most recent data that the mobile device 504 has stored (e.g., a timestamp of the most recent data from the inhalation device 100 that is stored on the mobile device 504). If the inhalation device 100 has more recent data (e.g., data with a timestamp that is more recent than that indicated by the request), then the inhalation device 100 may transmit the more recent data to the mobile device 504. Thereafter, the mobile device 504 that receives the more recent data may upload that data to the DHP 510. Then, the other of the mobile devices that didn't receive the more recent data directly from the inhalation device 100 (e.g., such as the mobile devices 502, 506), may receive the more recent data from the DHP 510, for example, as described below. For example, when a user logs into a mobile application on the other mobile devices, the mobile application may cause the mobile device to retrieve the data (e.g., all, recent data) from the DHP 510, rather than from the inhalation device 100. As such, the mobile applications on the other mobile devices may not request the data from the inhalation device 100, because those mobile devices have already received the data from the DHP 510.

Accordingly, the inhalation device 100 may be configured to limit the number of times it transfers the data to a mobile device (e.g., which may be any of the mobile devices, and which may be a different mobile device during each data transfer). In this example, the mobile device is limited to a single transfer of stored data, because, for example, once that data is provided to a single external device, the external device transfers the data to the DHP 510, and the DHP 510 transfer the data to all other authorized external devices. If the mobile device was not limited to a single transfer of stored data, however, the same instance of stored data may be transferred to the DHP 510 multiple times, which may negatively affect the integrity and/or validity of the data in the DHP 510 (e.g., as multiple instances of the same data may exist in the DHP 510).

More specifically, the DHP 510 may be configured to enable, and in some instances initiate, the transfer of data from the mobile devices 502, 504, 506. For example, the DHP 510 may expose a REST API to the processors and/or mobile applications residing on the mobile devices 502, 504, 506. The mobile devices 502, 504, 506 may send any data related to an inhalation device 100 that has not already been uploaded to the DHP 510, and with this data send any combination of an indication of the associated user and/or the timestamp for the data (which may include the local time and time zone of the mobile devices). In some examples, the mobile devices 502, 504, 506 may be configured to send inhalation data (or an indication that there is no new inhalation data) to the DHP 510 periodically, such as every 15 minutes. The DHP 510 may also store incoming data from the computers 512. The DHP 510 may receive the patient's consent via their respective mobile devices 502, 504, 506.

The DHP 510 may transmit data, such as inhaler data, to one or more of the mobile devices 502, 504, 506. For example, the DHP 510 may receive data from one mobile device, and then transmit that data to the other mobile device(s) associated with that user, for example, when the other mobile device(s) don't already have that inhaler data. In some examples, the mobile devices 502, 504, 506 may transmit a request to the DHP 510 (e.g., periodically, such as every 15 minutes) for all new inhaler data associated with a user. The request may include an indication of the user and at least one of an inhaler or a medicament type (e.g., a rescue medicament type or a maintenance medicament type). The request may also include an indication of the last synchronization time between that mobile device and the inhaler, regardless of whether any new inhaler related data was communicated from the inhaler to the mobile device. The last synchronization time for a mobile device may indicates the most recent time the inhaler was connected with that mobile device, regardless of whether any new inhaler related data was communicated from the inhaler to the mobile device. The DHP 510 may receive the request, determine the user, the inhaler, and/or the medicament type, and determine the last synchronization time between the mobile device and the inhaler. The DHP 510 may then determine whether it has stored any data (e.g., usage events) that postdate (come after) the synchronization time indicated by the request by comparing the associated timestamps with the last synchronization time provided in the request. If there is data for that inhaler that comes after the last synchronization time, the DHP 510 is configured to send the data and associated timestamps to the mobile device (e.g., with any combination of data that indicates the associated user, the inhaler, and/or medicament type). The data sent by the DHP 510 may include the data from the inhaler, such as a usage event, along with a timestamp of the data (e.g., including the local mean time and time zone of the event), inhaler information such as data indicating the medicament type and/or dosage, and data indicating the user associated with the event.

Further, in some examples, the DHP 510 may return additional data relating to the user and/or the medicament, such as profile information relating to the user, the prescription order information, user preferences, questionnaire responses, etc. For example, the request may include an additional field that indicates a last synchronization time between the mobile device and the inhalation device 100 or between the mobile device and the DHP 510 where information other than inhaler related data, such as usage events, was received by the mobile device. The DHP 510 may then determine whether it has stored any other data, such as that described above, that postdate the synchronization time indicated by the request, and if so, send the other data and associated timestamps (e.g., in combination with any combination of the associated user, the inhaler, and medicament type) to the mobile device.

As such, the system 500 may be configured to limit the number of times that an inhalation device 100 has to communicate its data to a mobile device, while also ensuring that multiple mobile devices 502, 504, 506 associated with the inhalation device 100 have the most recent data associated with the inhalation device 100 and/or the user, regardless of the number of mobile devices 502, 504, 506 associated with the inhalation device 100 and/or the user. This is particularly true in examples where the mobile device is configured to send new data received from the inhalation device 100 and/or an indication of a last synchronization between the mobile device and the inhalation device 100 to the DHP periodically, and also send requests to the DHP for new data not already stored on the mobile device periodically.

Further, the DHP 510 may cause the computer 512 associated with the health care provider to provide inhaler data to practitioners and health care professionals to allow them to view inhaler data specific to a program to which a patient has consented. In one example, the DHP 510 causes the computer 512 associated with the health care provider to provide the inhalation data via a graphical user interface (GUI) that is presented on a display device associated with the health care provider's computer.

The DHP 510 may define any number of programs, which in some instances may be configured and altered by a health care provider. When providing inhaler data to a health care provider, the DHP 510 may generate an alert (e.g., generate and provide a GUI) that is specific to a particular program associated with that health care provider. A program defines a set of criteria, such as types of medications (e.g., any combination of rescue and/or maintenance medications), specific patients and in turn their applicable inhalers, other users of the programs such as particular physicians, practice groups, and/or administrators, the types of data presented to the health care provider such as charts, event tables, usage summaries, etc. The health care provider may configure and establish any number of programs using the DHP 510. Further, a particular patient and their inhalers may be associated with any number of unique programs. In some examples, the programs are stored and maintained by the DHP 510, and the computer 512 associated with the health care provider is configured to access the data relevant to each program from the DHP 510 using, for example, an application, such as a dashboard or web application. In such examples, and once a program is established, the DHP 510 is configured to receive inhaler data associated with the program, analyze and manipulate the inhaler data to the extent necessary, and provide program data (e.g., via the dashboard) to the health care provider. The program data may include inhaler data that is specific to the configuration of a particular program, and for example, additional data that is derived from the inhaler data, as is described in more detail below. For example, the DHP 510 may enable a GUI, such as those described herein, on the computer 512 associated with the health care provider that presents the program data to the health care provider.

For example, the DHP 510 may include a dashboard application that may be accessible by the computer 512 associated with a health care provider. In some examples, the dashboard application is a web application (e.g., a web portal). For example, the DHP 510 is configured to provide data, such as inhaler data, to clinicians and physicians through the use of the dashboard application (e.g., via a REST API). The DHP 510 may cause the computer 512 associated with the health care provider to provide inhaler data to practitioners and health care professionals to allow them to view inhaler data specific to a program to which a patient has consented. In one example, the DHP 510 causes the computer 512 associated with the health care provider to provide the inhalation data via a graphical user interface (GUI) that is presented on the health care provider's computer.

Alternatively or additionally, in some examples, after the mobile device 504 receives the more recent data from the inhalation device 100 and uploads that data to the DHP 510, the mobile application may be configured to cause the mobile device to transmit a notification to the inhalation device 100 indicating that the inhalation data was uploaded to the DHP 510. Accordingly, upon receiving the notification that the inhalation data has been uploaded to the DHP 510, the inhalation device 100 may be configured to not upload that data to another mobile application, even if it receives a request for that data. The mobile application may, however, be configured to transmit, to a mobile device, inhalation data that postdates the data that was uploaded to the DHP 510.

Alternatively or additionally, in some examples, the system 100 may be configured such that the inhalation device 100 may only transfer data to one, single mobile device. For example, when the mobile application on the mobile device 504 (e.g., initially) connects to and/or receives data from the inhalation device 100, the inhalation device 100 may receive and store an ID associated with the mobile device 504. After receiving the ID, the inhalation device 100 may be restricted to connecting and transferring data to the mobile device 504 and/or to any other device with the same ID. If other external devices, such as the mobile devices 502, 506, attempt to connect to the inhalation device 100, the inhalation device 100 does not transfer data if such devices have a different ID. Accordingly, the electronics module 120 may conserve power by limiting the instances in which it connects to external devices and transmits data collected by the sensor system 128, for example.

All or a portion of the data transferred to the mobile device 504 may be communicated by the device 504 to a DHP 510. The data may be stored in the DHP 510 where it may be later accessed or retrieved by the mobile application on the mobile device 504 and/or by a computer 512 associated with the health care provider. The data may also be accessed or retrieved by the respective mobile applications on the mobile devices 502, 506. Accordingly, the child and the child's father may still be able to monitor usage and/or other conditions associated with the inhalation device 100 on their respective mobile devices 502, 506 even though the inhalation device 100 may be restricted to connecting with and/or transferring data to the mobile device 504.

Further, in some examples, the inhalation device 100 may limit how often it communicates data with an external device (e.g., a mobile device), for example, when the inhalation device 100 is in connected mode. This may allow the inhalation device 100 to save battery power, for example, while in connected mode. The communication protocol enabled by the inhalation device 100 may, for example, include a parameter that defines how often the inhalation device 100 will accept requests for data while in connected mode. The parameter may, for instance, allow the inhalation device 100 to skip connection events without the external device dropping the connection, and as such, the inhalation device 100 may remain in connected mode even though it skips connections events. In such examples, the inhalation device 100 may set this parameter to its maximum value. For example, if the inhalation device 100 communicates using BLE, the inhalation device 100 may configure the parameter "connSlaveLatency" to a maximum value (e.g., every 2 seconds, every 4 seconds, etc.).

Further, in some examples, the inhalation device 100 does not include an actuator, button, or switch to initiate a pairing process with a mobile device. The inhalation device 100 may, however, include other means for facilitating the pairing process. For example, the inhalation device 100 may include a barcode, such as a Quick Response (QR) code 160. Although described as a QR code, other types of barcodes may be used. The use of the QR code to initiate the pairing process may further reduce the required battery/power consumption of the electronics module 120 of the inhalation device 100. Further, although the QR code 160 is illustrated as being located on the top of the top cap 102 of the inhalation device 100, in other examples, the inhalation device 100 may include a QR code that is located elsewhere on the inhalation device 100, such as on the main housing 104 or on the mouthpiece cover 108. The mobile device may include a camera, and the mobile application residing on the mobile device may be configured to access the camera and read the QR code 160.

The QR code 160 may include (e.g., be coded to indicate) various types of information associated with the inhalation device 100. The QR code 160 may include a BLE passkey that is unique to the inhalation device 100. Upon reading or scanning the QR code 160 using the camera, the mobile application may determine the BLE passkey associated with the device 100 and complete an authentication process, thereby enabling it to communicate with the electronics module 120 using the BLE passkey. If the communications session is subsequently lost because, for example, the inhalation device 100 moves out of range, the mobile device may be configured to use the BLE passkey to automatically pair with the electronics module 120 without using the QR code 160 when the inhalation device 100 is back within range.

Further, in some examples, the QR code 160 may include an indication of the type of the inhalation device 100 (e.g., the medication type, the number of doses, the strength, the dosing schedule, etc.). Table 1 provides a non-limiting example of the identifiers included in the QR code 160 for various inhalation devices 100.

TABLE 1

| Identifier in QR code | Brand of inhaler | Medicament | Dose strength (mcg) | Total dose count of inhaler prior to use | Medicament identification number |
|---|---|---|---|---|---|
| <blank> | ProAir Digihaler | albuterol | 117 | 200 | AAA200 |
| AAA030 | ProAir Digihaler | albuterol | 117 | 30 | AAA030 |
| FSL060 | AirDuo Digihaler | fluticasone/ salmeterol | 55/14 | 60 | FSL060 |
| FSM060 | AirDuo Digihaler | fluticasone/ salmeterol | 113/14 | 60 | FSM060 |
| FSH060 | AirDuo Digihaler | fluticasone/ salmeterol | 232/14 | 60 | FSH060 |
| FPL060 | ArmonAir Digihaler | fluticasone | 55 | 60 | FPL060 |
| FPM060 | ArmonAir Digihaler | fluticasone | 113 | 60 | FPM060 |
| FPH060 | ArmonAir Digihaler | fluticasone | 232 | 60 | FPH060 |

As shown in Table 1, the identifier further denotes the dose strength and the total dose count of the inhaler prior to use. The mobile application residing on the mobile device may use the information identifier by the identifier to, in combination with the usage information, control a user interface of the mobile device to issue a notification when the label recommended dosages have been exceeded, as previously described. Alternatively or additionally, the mobile application residing on the mobile device may use the total dose count of the inhaler prior to use and the usage information to determine the number of doses remaining in the respective inhalation device 100.

The QR code 160 on the inhalation device 100 may, for instance, further comprise a security key, for example in the form of a series of alphanumerical characters, for preventing unauthorized users from accessing the respective inhalation device 100. The mobile application residing on the mobile device may be able to decrypt the respective encrypted data once the mobile application has been provided with the security key, but may not be able to decrypt the respective encrypted data before the mobile application has been provided with the security key. More generally, the security key may be included in the respective identifier.

In a non-limiting example, the system is configured to restrict one or more, e.g. each, of the inhalers included in the system to a single user account.

In such an example, a passkey, e.g. provided in the QR code, may allow synchronization between the respective inhalation device 100 and mobile applications of the system. The passkey and, in turn, the usage parameter data, e.g. inhalation and/or usage data, from the respective inhalation device may be public. This public inhalation data may not be associated with the particular subject until synchronization with the single user account.

Since the system is configured to restrict the respective inhaler to being associated with the single user account, the respective inhaler may be prevented from being synchronized with another user account, for example in situations where the inhaler is lost or stolen. In this way, third parties may be prevented from acquiring usage parameter data which is not theirs.

Accordingly, the mobile application can determine the type of inhalation device 100 when receiving the QR code 160 (e.g., the medicament type, the dosage strength, and the number of doses), and prior to the first use of the inhalation device 100 by a user. For examples, the mobile application may receive (e.g., capture) an image of the QR code using the camera of the mobile device. The mobile application may then decode the image of the QR code to acquire the data stored within the QR code. In some examples, the QR code 160 may comprise a multi-digit alphanumeric code, such as a six digit code (e.g., ssm060, aaa200, etc.) that indicates the type of the inhalation device 100. For example, the multi-digit alphanumeric code may be a unique drug product identifier (e.g., product ID) of the inhalation device 100. Accordingly, the QR code 160 may directly communicate the type of the inhalation device 100 (e.g., the medication type, the number of doses, the strength, the dosing schedule, etc.) via the multi-digit alphanumeric code provided via the QR code 160 (e.g., and as such, the mobile application does not have to access a website using the QR code 160 to acquire the type of the inhalation device). A multi-digit alphanumeric code of "AAA030" may, for example, indicate that the medication type is albuterol, the strength is 117 mcg, and the number of doses is 30.

In some examples, the BLE passkey provided via the QR code 160 may comprise the multi-digit alphanumeric, for example. Further, in some embodiments, the QR code 160 may not directly indicate, to the mobile application, the information relating to the medication type, the number of doses, the strength, the dosing schedule, etc. of the inhalation device 100. Rather, the QR code 160 may comprise information that can be used by the mobile application to acquire such information relating to the inhalation device 100 from a remote device (e.g., a cloud-based system, such as a remote server).

Moreover, in some examples, the QR code 160 may include any combination of a serial number of the inhalation device 100, a hardware revision number of the inhalation device 100, and/or a software revision number of the inhalation device 100. Further, although described with reference to a QR code 160, the inhalation device 100 may include any code (e.g., barcode) that indicates the type of the inhalation device 100, a communication passkey (e.g., BLE passkey), a manufacturer name of the inhalation device 100, a serial number of the inhalation device 100, a hardware revision number of the inhalation device 100, a software revision number of the inhalation device 100, and/or the like.

Upon receiving the QR code 160, the mobile application may determine the details of the inhalation device 100 (e.g., the medication type, the number of doses, the strength, the dosing schedule, etc.), such as directly through a multi-digit alphanumeric provided via the QR code 160. Alternatively or additionally, in some example, the mobile application may be configured to send a request (e.g., that includes the multi-digit alphanumeric code) to a DHP 510 for the details relating to the inhalation device 100 (e.g., the medication type, the number of doses, the strength, the dosing schedule, etc.). This can be particular important, for example, in instances where mislabeling issues can arise, and the inhalation device 100 is mislabeled with the incorrect type of medication. The use of the QR code 160 allows for accurate details relating to the inhalation device 100 to be acquired by the mobile application prior to the user using the inhalation device 100, for example. This may, for example, help prevent issues relating to incorrect dosage reminders based on incorrect dosing schedules, incorrect refill warning, etc. that could otherwise have been determined based on the incorrect medication labeling on the inhalation device 100. Further, in some examples, the mobile application may determine that the user associated with the mobile application is not prescribed the medication and/or dose strength indicated by the QR code. For instance, the mobile application may send the medication type or the strength of the inhaler indicated by the QR code to the DHP 510, and in response, may receive an indication of the user's compatibility with the medication type or the strength of the inhaler from the cloud-based server (e.g., such as a direct compatible or not compatible message, or an indication of the medication types and strengths associated with the user). For example, the mobile application may request and receive the user's prescription information from the DHP 510. And the mobile application may generate an alert (e.g., a GUI displayed on the mobile device and/or at the computer associated with the HCP) that indicates that the user has the incorrect inhaler, either based on the medicament type or strength, as indicated by the QR code. Further, in such instances, the mobile application may reject the pairing process with the inhalation device 100.

Further, in some examples, the mobile application may be used with specific types of inhalation devices, but not all. Accordingly, the mobile application may display an error message if the information provided by the QR code 160 indicates that that the inhalation device 100 is not an inhalation device that is compatible with the mobile application. Further, the mobile application may provide a link to a mobile application store to download the correct mobile application for the type of inhalation device 100. If, for example, the mobile application determines that the inhalation device is not the compatible with the mobile application (e.g., based on the QR code 160 or multi-digit alphanumeric code), the mobile application may reject the pairing process of the inhalation device 100 with the mobile device (e.g., before data transfer or a first use of the inhalation device 100). If the mobile application determines that the inhalation device is the compatible with the mobile application (e.g., based on the QR code 160 or multi-digit alphanumeric code), the mobile application may accept or allow the pairing process of the inhalation device 100 with the mobile device.

Figure 6:
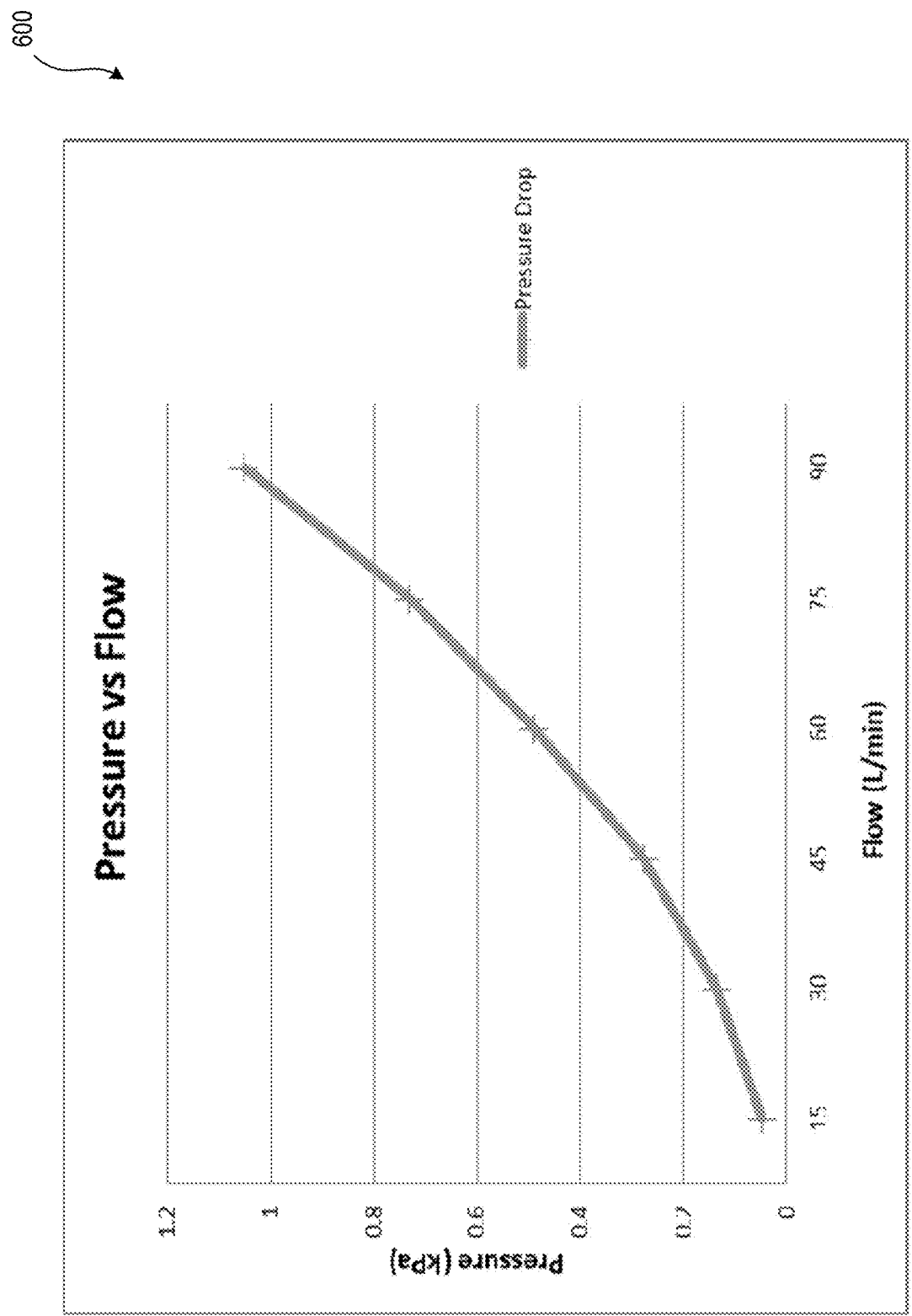
FIG. 6 is a graph of example airflow rates versus pressure.

FIG. 6 is a graph 600 of example airflow rates versus pressure. The airflow rates and profile shown in FIG. 6 are merely examples and the determined rates may depend on the size, shape, and design of the inhalation device 100 and its components.

The electronics module 120 may generate data (e.g., usage events) by comparing signals received from the sensor system 128 and/or the determined airflow metrics to one or more thresholds or ranges, for example, as part of an assessment of how the inhalation device 100 is being used and/or whether the use is likely to result in the delivery of a full dose of medication. For example, where the determined airflow metric corresponds to an inhalation with an airflow rate below a particular threshold, the electronics module 120 may determine that there has been no inhalation or an insufficient inhalation from the mouthpiece 106 of the inhalation device 100. If the determined airflow metric corresponds to an inhalation with an airflow rate above a particular threshold, the electronics module 120 may determine that there has been an excessive inhalation from the mouthpiece 106. If the determined airflow metric corresponds to an inhalation with an airflow rate within a particular range, the electronics module 120 may determine that the inhalation is "good", or likely to result in a full dose of medication being delivered. The electronics module 120 may associate a timestamp with the data.

The pressure measurement readings and/or the computed airflow metrics may be indicative of the quality or strength of inhalation from the inhalation device 100. For example, when compared to a particular threshold or range of values, the readings and/or metrics may be used to categorize the inhalation as a certain type of event, such as a good inhalation event, a low inhalation event, a no inhalation event, or an excessive inhalation event. The categorization of the inhalation may be usage parameters stored as personalized data of the subject.

The no inhalation event may be associated with pressure measurement readings and/or airflow metrics below a particular threshold, such as an airflow rate less than or equal to 30 Lpm. The no inhalation event may occur when a subject does not inhale from the mouthpiece 106 after opening the mouthpiece cover 108 and during the measurement cycle. The no inhalation event may also occur when the subject's inspiratory effort is insufficient to ensure proper delivery of the medication via the flow pathway 119, such as when the inspiratory effort generates insufficient airflow to activate the deagglomerator 121 and, thus, aerosolize the medication in the dosing cup 116.

The low inhalation event may be associated with pressure measurement readings and/or airflow metrics within a particular range, such as an airflow rate greater than 30 Lpm and less than or equal to 45 Lpm. The low inhalation event may occur when the subject inhales from the mouthpiece 106 after opening the mouthpiece cover 108 and the subject's inspiratory effort causes at least a partial dose of the medication to be delivered via the flow pathway 119. That is, the inhalation may be sufficient to activate the deagglomerator 121 such that at least a portion of the medication is aerosolized from the dosing cup 116.

The good inhalation event may be associated with pressure measurement readings and/or airflow metrics above the low inhalation event, such as an airflow rate which is greater than 45 Lpm and less than or equal to 200 Lpm. The good inhalation event may occur when the subject inhales from the mouthpiece 106 after opening the mouthpiece cover 108 and the subject's inspiratory effort is sufficient to ensure proper delivery of the medication via the flow pathway 119, such as when the inspiratory effort generates sufficient airflow to activate the deagglomerator 121 and aerosolize a full dose of medication in the dosing cup 116.

The excessive inhalation event may be associated with pressure measurement readings and/or airflow metrics above the good inhalation event, such as an airflow rate above 200 Lpm. The excessive inhalation event may occur when the subject's inspiratory effort exceeds the normal operational parameters of the inhalation device 100. The excessive inhalation event may also occur if the device 100 is not properly positioned or held during use, even if the subject's inspiratory effort is within a normal range. For example, the computed airflow rate may exceed 200 Lpm if the air vent is blocked or obstructed (e.g. by a finger or thumb) while the subject is inhaling from the mouthpiece 106.

Any suitable thresholds or ranges may be used to categorize a particular event. Some or all of the events may be used. For example, the no inhalation event may be associated with an airflow rate which is less than or equal to 45 Lpm and the good inhalation event may be associated with an airflow rate which is greater than 45 Lpm and less than or equal to 200 Lpm. As such, the low inhalation event may not be used at all in some cases.

The pressure measurement readings and/or the computed airflow metrics may also be indicative of the direction of flow through the flow pathway 119 of the inhalation device 100. For example, if the pressure measurement readings reflect a negative change in pressure, the readings may be indicative of air flowing out of the mouthpiece 106 via the flow pathway 119. If the pressure measurement readings reflect a positive change in pressure, the readings may be indicative of air flowing into the mouthpiece 106 via the flow pathway 119. Accordingly, the pressure measurement readings and/or airflow metrics may be used to determine whether a subject is exhaling into the mouthpiece 106, which may signal that the subject is not using the device 100 properly.

The inhalation device 100 may include a spirometer or similarly operating device to enable measurement of lung function metrics. For example, the inhalation device 100 may perform measurements to obtain metrics related to a subject's lung capacity. The spirometer or similarly operating device may measure the volume of air inhaled and/or exhaled by the subject. The spirometer or similarly operating device may use pressure transducers, ultrasound, or a water gauge to detect the changes in the volume of air inhaled and/or exhaled.

The data collected from, or calculated based on, the usage of the inhalation device 100 (e.g. pressure metrics, airflow metrics, lung function metrics, dose confirmation information etc.) may be computed and/or assessed via external devices as well (e.g. partially or entirely). More specifically, the wireless communication circuit 129 in the electronics module 120 may include a transmitter and/or receiver (e.g. a transceiver), as well as additional circuitry.

For example, the wireless communication circuit 129 may include a Bluetooth chip set (e.g. a Bluetooth Low Energy chip set), a ZigBee chipset, a Thread chipset, etc. As such, the electronics module 120 may wirelessly provide the data, such as pressure measurements, airflow metrics, lung function metrics, dose confirmation information, and/or other conditions related to usage of the inhalation device 100, to a mobile device. The electronics module 120 may also send the timestamps associated with the data. The data may be provided in real time to the external device to enable exacerbation risk prediction based on real-time data from the inhalation device 100 that indicates time of use, how the inhalation device 100 is being used, and personalized data about the subject, such as real-time data related to the subject's lung function and/or medical treatment. The external device may include software for processing the received information and for providing compliance and adherence feedback to the subject via a graphical user interface (GUI), such as via a mobile device or via a computer associated with a HCP.

The airflow metrics may include personalized data that is collected from the inhalation device 100 in real-time, such as one or more of an average flow of an inhalation/exhalation, a peak flow of an inhalation/exhalation (e.g. a maximum inhalation received), a volume of an inhalation/exhalation, a time to peak of an inhalation/exhalation, and/or the duration of an inhalation/exhalation. The airflow metrics may also be indicative of the direction of flow through the flow pathway 119. That is, a negative change in pressure may correspond to an inhalation from the mouthpiece 106, while a positive change in pressure may correspond to an exhalation into the mouthpiece 106. When calculating the airflow metrics, the electronics module 120 may be configured to eliminate or minimize any distortions caused by environmental conditions. For example, the electronics module 120 may re-zero to account for changes in atmospheric pressure before or after calculating the airflow metrics. The one or more pressure measurements and/or airflow metrics may be timestamped and stored in the memory of the electronics module 120.

In addition to the airflow metrics, the inhalation device 100, or another computing device, may use the airflow metrics to generate additional data. For example, the controller of the electronics module 120 of the inhalation device 100 may translate the airflow metrics into other metrics that indicate the subject's lung function and/or lung health that are understood to medical practitioners, such as peak inspiratory flow metrics, peak expiratory flow metrics, and/ or forced expiratory volume in 1 second (FEV1), for example. The electronics module 120 of the inhaler may determine a measure of the subject's lung function and/or lung health using a mathematical model such as a regression model. The mathematical model may identify a correlation between the total volume of an inhalation and FEV1. The mathematical model may identify a correlation between peak inspiratory flow and FEV1. The mathematical model may identify a correlation between the total volume of an inhalation and peak expiratory flow. The mathematical model may identify a correlation between peak inspiratory flow and peak expiratory flow.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

What is claimed is:

1. A system comprising:
    a cloud-based server comprising a processor, memory, and a communication circuit;
    an inhaler comprising a mouthpiece, medicament, and an electronics module, the electronics module comprising a processor, memory, and a communication circuit;
    a first mobile application residing on a first mobile device, the first mobile device comprising a processor, a communication circuit, and memory, and the first mobile application configured to cause the processor of the first mobile device to:
        send a request for inhalation data to the inhaler;
        receive the inhalation data from the inhaler, the inhalation data associated with a timestamp; and
        transmit the inhalation data and timestamp to the cloud-based server; and
    a second mobile application residing on a second mobile device, the second mobile device comprising a processor, a communication circuit, and memory, and the second mobile application configured to cause the processor of the second mobile device to:
        transmit a request to the cloud-based server that includes a timestamp of the most recent inhalation data of the inhaler that is stored on the second mobile device in response to entering a connected mode with the inhaler and prior to causing the second mobile device to transmit a request for inhalation data to the inhaler; and
        receive the inhalation data of the inhaler from the cloud-based server in response to the request, wherein the timestamp associated with the inhalation data is subsequent to the timestamp of the most recent inhalation data of the inhaler that is stored on the second mobile device.

2. The system of claim 1, wherein the system is configured to limit the number of times the inhaler transmits the inhalation data to any mobile device to a single time.

3. The system of claim 1, wherein the second mobile application is configured to cause the second mobile device to transmit a product identification (ID) associated with the inhaler or a patient ID associated with a patient of the inhaler to the cloud-based server prior to the second mobile application receiving the inhalation data of the inhaler from the cloud-based server.

4. The system of claim 1, wherein the second mobile application is configured to cause the processor of the second mobile device to periodically transmit the request to the cloud-based server that comprises the timestamp of the most recent inhalation data of the inhaler that is stored on the second mobile device.

5. The system of claim 1, wherein the second mobile application is configured to cause the second mobile device to transmit a request to the inhaler, receive second inhalation data from the inhaler, and transmit the second inhalation data and an associated timestamp to the cloud-based server; and
    wherein the first mobile application is configured to transmit a request to the cloud-based server that includes an indication of a last synchronization time between the first mobile application and the inhaler, and receive the second inhalation data and the associated timestamp of the inhaler from the cloud-based server, wherein the timestamp associated with the second inhalation data is subsequent to the last synchronization time between the first mobile application and the inhaler.

6. The system of claim 1, wherein the electronics module of the inhaler is configured to:
   start a counter in response to the electronics module being changed from an off state to an active state for the first time;
   record the inhalation data in response to a use of the inhaler by the user;
   associate a counter value with the inhalation data; and
   send the inhalation data and the counter value to the first mobile device; and
   wherein the first mobile application is configured to cause the processor of the first mobile device to determine the timestamp using the counter value, wherein the timestamp indicates a local mean time of the inhalation data based on the time zone of the first mobile device.

7. The system of claim 1, wherein the inhaler is configured to dispense discrete doses of the medicament, and wherein the medicament comprises one of:
   albuterol sulfate, 117 microgram (mcg) of albuterol sulfate per discrete dose;
   fluticasone propionate, 55 mcg, 113 mcg, or 232 mcg of fluticasone propionate per discrete dose; or
   fluticasone propionate combined with salmeterol xinafoate, 55 mcg, 113 mcg, or 232 mcg of fluticasone propionate, and 14 mcg of salmeterol xinafoate per discrete dose.

8. The system of claim 1, wherein the medicament comprises one of albuterol sulfate, fluticasone propionate or furoate, beclomethasone dipropionate, or fluticasone propionate or furoate combined with salmeterol.

9. The system of claim 1, wherein the inhaler further comprise a Quick Response (QR) code; and
   wherein the first mobile device further comprises a camera, and the first mobile application is configured to cause the processor of the first mobile device to:
   receive an image of the QR code of the inhaler using the camera of the first mobile device;
   determine a product identifier (ID) of the inhaler based on the image of the QR code;
   determine a dosing schedule of the inhaler using the product ID; and
   generate an alert indicating that a scheduled dose is due based on the dosing schedule of the inhaler.

10. A system comprising:
    a cloud-based server comprising a processor, memory, and a communication circuit;
    an inhaler comprising a mouthpiece, medicament, and an electronics module, the electronics module comprising a processor, memory, and a communication circuit;
    a first mobile application residing on a first mobile device, the first mobile device comprising a processor, a communication circuit, and memory, and the first mobile application configured to cause the processor of the first mobile device to:
    send a request for inhalation data to the inhaler;
    receive the inhalation data from the inhaler, the inhalation data associated with a timestamp; and
    transmit the inhalation data and timestamp to the cloud-based server; and
    a second mobile application residing on a second mobile device, the second mobile device comprising a processor, a communication circuit, and memory, and the second mobile application configured to cause the processor of the second mobile device to:
    transmit a request to the cloud-based server for the inhalation data of the inhaler in response to detecting a user login event to the second mobile application and prior to causing the second mobile device to transmit a request for the inhalation data to the inhaler; and
    receive the inhalation data of the inhaler from the cloud-based server in response to the request.

11. The system of claim 10, wherein the inhaler further comprise a Quick Response (QR) code; and
    wherein the first mobile device further comprises a camera, and the first mobile application is configured to cause the processor of the first mobile device to:
    receive an image of the QR code of the inhaler using the camera of the first mobile device, wherein the QR code provides a product identifier (ID) of the inhaler;
    determine one or more of a medication type or a strength of the medication based on the product identifier;
    determine that the inhaler is not compatible with the first mobile application or the user based on the medication type or the strength of the inhaler; and
    generate an error message on a display device of the first mobile device based on the inhaler being not compatible with the mobile application or the user.

12. The system of claim 11, wherein the first mobile application is configured to cause the processor of the first mobile device to:
    send the medication type or the strength of the inhaler to the cloud-based server; and
    receive an indication of the user's compatibility with the medication type or the strength of the inhaler from the cloud-based server.

13. The system of claim 11, wherein the first mobile application is further configured to cause the processor of the first mobile device to reject a pairing process of the inhaler with the first mobile device based on the inhaler being not compatible with the first mobile application.

14. The system of claim 10, wherein the inhaler further comprise a Quick Response (QR) code, but the inhaler does not comprise an actuator, button, or switch to initiate a communication pairing process with the first mobile device.

15. The system of claim 14, wherein the first mobile application is further configured to cause the processor of the first mobile device to:
    receive an image of the QR code of the inhaler using a camera of the first mobile device;
    determine a communication passkey that is unique to the inhaler based on the QR code; and
    transmit the communication passkey to the electronics module of the inhaler to enable communication between the electronics module and the first mobile application.

16. The system of claim 15, wherein the communication passkey comprises a product identifier and a Bluetooth Low Energy (BLE) passkey.

17. The system of claim 10, wherein the second mobile application is configured to cause the second mobile device to transmit a product identification (ID) associated with the inhaler or a patient ID associated with a patient of the inhaler to the cloud-based server prior to the second mobile application receiving the inhalation data of the inhaler from the cloud-based server.

18. The system of claim 10, wherein in response to entering a connected mode with the inhaler, the second mobile application is configured to cause the second mobile device to transmit the request to the cloud-based server prior to causing the second mobile device to transmit a request for inhalation data to the inhaler.

19. The system of claim 10, wherein the system is configured to limit the number of times the inhaler transmits the inhalation data to any mobile device to a single time.

20. The system of claim 10, wherein the second mobile application is configured to cause the processor of the second mobile device to periodically transmit a request to the cloud-based server that comprises a timestamp of the most recent inhalation data of the inhaler that is stored on the second mobile device.

21. The system of claim 10, wherein the inhaler further comprise a Quick Response (QR) code; and
    wherein the first mobile device further comprises a camera, and the first mobile application is configured to cause the processor of the first mobile device to:
    receive an image of the QR code of the inhaler using the camera of the first mobile device;
    determine a product identifier (ID) of the inhaler based on the image of the QR code;
    determine a dosing schedule of the inhaler using the product ID; and
    generate an alert indicating that a scheduled dose is due based on the dosing schedule of the inhaler.

22. A system comprising:
    a cloud-based server comprising a processor, memory, and a communication circuit;
    an electronics module configured to be attached to and removed from an inhaler, the electronics module comprising a processor, memory, and a communication circuit;
    a first mobile application residing on a first mobile device, the first mobile device comprising a processor, a communication circuit, and memory, and the first mobile application configured to cause the processor of the first mobile device to:
    send a request for usage data to the electronics module;
    receive the usage data from the electronics module, the usage data associated with a timestamp; and
    transmit the usage data and timestamp to the cloud-based server; and
    a second mobile application residing on a second mobile device, the second mobile device comprising a processor, a communication circuit, and memory, and the second mobile application configured to cause the processor of the second mobile device to:
    transmit a request to the cloud-based server for the usage data of the electronics module in response to detecting a user login event to the second mobile application and prior to causing the second mobile device to transmit a request for the usage data to the electronics module; and
    receive the usage data of the inhaler from the cloud-based server in response to the request.

23. The system of claim 22, wherein the second mobile application is configured to cause the second mobile device to transmit a product identification (ID) associated with the electronics module or a patient ID associated with a patient of the electronics module to the cloud-based server prior to the second mobile application receiving the usage data of the electronics module from the cloud-based server.

24. The system of claim 22, wherein the second mobile application is configured to cause the processor of the second mobile device to periodically transmit a request to the cloud-based server that comprises a timestamp of the most recent usage data of the electronics module that is stored on the second mobile device.

* * * * *